(12) United States Patent
Guba et al.

(10) Patent No.: US 7,253,197 B2
(45) Date of Patent: Aug. 7, 2007

(54) AMINOTHIAZOLE DERIVATIVES

(75) Inventors: Wolfgang Guba, Mullheim (DE); Patrizio Mattei, Riehen (CH); Werner Neidhart, Hagenthal le Bas (FR); Matthias Heinrich Nettekoven, Grenzach-Wyhlen (DE); Philippe Pflieger, Schwoben (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 7 days.

(21) Appl. No.: 10/634,431

(22) Filed: Aug. 5, 2003

(65) Prior Publication Data
US 2004/0038990 A1 Feb. 26, 2004

(30) Foreign Application Priority Data
Aug. 7, 2002 (EP) .................................. 02017677

(51) Int. Cl.
*A61K 31/426* (2006.01)
*A61K 31/427* (2006.01)
*C07D 277/42* (2006.01)
*C07D 401/12* (2006.01)

(52) U.S. Cl. ...................... 514/370; 514/255; 514/342; 544/405; 546/270.7; 548/194

(58) Field of Classification Search ................ 548/194; 546/270.7; 544/405; 514/370, 342, 255.05, 514/255

See application file for complete search history.

(56) References Cited

U.S. PATENT DOCUMENTS

| 4,035,367 | A | | 7/1977 | Simpson |
| 4,598,089 | A | | 7/1986 | Hadvary et al. |
| 4,649,146 | A | * | 3/1987 | Takaya et al. ............... 514/307 |
| 4,931,463 | A | | 6/1990 | Barbier et al. |
| 4,983,746 | A | | 1/1991 | Barbier et al. |
| 5,399,720 | A | | 3/1995 | Karph et al. |
| 6,004,996 | A | | 12/1999 | Shah et al. |
| 6,573,263 | B2 | | 6/2003 | Niewohner et al. |
| 2001/0039275 | A1 | | 11/2001 | Bowler et al. |

FOREIGN PATENT DOCUMENTS

| EP | 185359 | 6/1986 |
| EP | 189577 | 8/1986 |
| EP | 443449 | 8/1991 |
| EP | 524495 | 1/1993 |
| WO | WO 96 37474 | 11/1996 |
| WO | WO 99 21845 | 5/1999 |
| WO | WO99/34786 | 7/1999 |
| WO | WO 99 62892 | 12/1999 |
| WO | WO 00/09122 | 2/2000 |
| WO | WO 00/09123 | 2/2000 |
| WO | WO 01 23389 | 4/2001 |
| WO | WO 01 64675 | 9/2001 |
| WO | WO 02 20488 | 3/2002 |
| WO | WO 02 094789 | 11/2002 |
| WO | WO 2003011843 | 2/2003 |

OTHER PUBLICATIONS

CA Registry No. 339023-15-3, May 30, 2001 ( entry date in Registry file on STN).*
CA Registry No. 339023-11-9, May 30, 2001 (entry date in Registry file on STN).*
CA Registry No. 339023-05-1, May 30, 2001 (entry date in Registry file on STN).*
CA Registry No. 339023-03-9, May 30, 2001 (entry date in Registry file on STN).*
CA Registry No. 339022-94-5, May 30, 2001 (entry date in Registry file on STN).*
CA Registry No. 339022-92-3, May 30, 2001 (entry date in Registry file on STN).*
CA Registry No. 339022-32-1, May 30, 2001 (entry date in Registry file on STN).*
CA Registry No. 339008-11-6, May 30, 2001 (entry date in Registry file on STN).*
Lin et al., Journal of Heterocyclic Chemistry, 16(7), pp. 1377-1383, (1979).*

* cited by examiner

*Primary Examiner*—Laura L. Stockton
(74) *Attorney, Agent, or Firm*—George W. Johnston; Dennis P. Tramaloni; Samuel H. Megerditchian

(57) ABSTRACT

Compounds of formula I

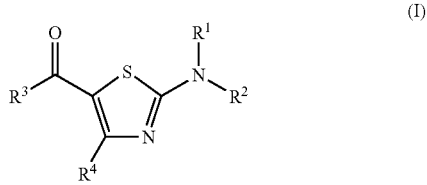

(I)

as well as pharmaceutically acceptable salts and esters thereof, wherein $R^1$ to $R^4$ have the significance given in the specification, and the compounds, salts and esters can be used for the treatment of obesity.

6 Claims, No Drawings

AMINOTHIAZOLE DERIVATIVES

BACKGROUND OF THE INVENTION

Neuropeptide Y is a 36 amino acid peptide that is widely distributed in the central and peripheral nervous systems. This peptide mediates a number of physiological effects through its various receptor subtypes. Studies in animals have shown that neuropeptide Y is a powerful stimulus of food intake, and it has been demonstrated that activation of neuropeptide Y Y5 receptors results in hyperphagia and decreased thermogenesis. Therefore compounds that antagonise neuropeptide Y at the Y5 receptor subtype represent an approach to the treatment of eating disorders such as obesity and hyperphagia.

The current approach is aiming at medical intervention to induce weight loss or prevention of weight gain. This is achieved by interfering with appetite control, which is mediated by the Hypothalamus, an important brain region proven to control food intake. Herein, neuropeptide Y (NPY) has been proven to be one of the strongest central mediators of food intake in several animal species. Increased NPY levels result in profound food intake. Various receptors of neuropeptide Y (NPY) have been described to play a role in appetite control and weight gain. Interference with these receptors is likely to reduce appetite and consequently weight gain. Reduction and long-term maintenance of body weight can also have beneficial consequences on co-associated risk factors such as arthritis, cardiovascular diseases, diabetes and renal failure.

SUMMARY OF THE INVENTION

The present invention provides novel thiazole derivatives useful as neuropeptide Y (NPY) receptor ligands, particularly neuropeptide Y (NPY) antagonists. The invention is concerned especially with compounds of formula

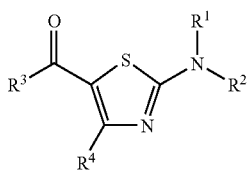

and pharmaceutically acceptable salts and esters thereof;
wherein
$R^1$ is aryl or heteroaryl, wherein at least one of the two meta positions of each aryl and heteroaryl group is substituted with $R^5$;
$R^2$ is hydrogen, alkyl or cycloalkyl;
$R^3$ is cycloalkyl, aryl or heteroaryl, wherein at least one of the two ortho positions of each cycloalkyl, aryl and heteroaryl group is substituted with $R^6$;
$R^4$ is hydrogen, alkyl or cycloalkyl;
$R^5$ is hydrogen, cyano, trifluoromethyl, alkyl-$SO_2$—, amino-$SO_2$—, halogen, alkoxy, alkylcarbonyl or aminocarbonyl;
$R^6$ is hydrogen, halogen, cyano, nitro, trifluoromethyl, alkyl, alkoxy, hydroxy or alkoxycarbonyl; and
with the proviso that one of $R^5$ and $R^6$ is not hydrogen.

The compounds of formula I and their pharmaceutically acceptable salts are neuropeptide ligands, for example neuropeptide receptor antagonists and in particular, they are selective neuropeptides Y Y5 receptor antagonists. The compounds of formula I and their pharmaceutically acceptable salts and esters can be used in the prophylaxis or treatment of arthritis, cardiovascular diseases, diabetes, renal failure and particularly eating disorders and obesity.

DETAILED DESCRIPTION OF THE INVENTION

The present invention provides novel thiazole derivatives useful as neuropeptide Y (NPY) receptor ligands, particularly neuropeptide Y (NPY) antagonists. The invention is concerned especially with compounds of formula

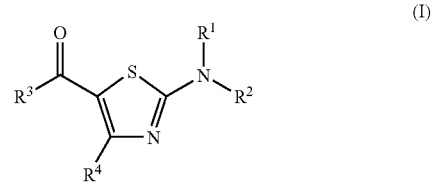

and pharmaceutically acceptable salts and esters thereof;
wherein
$R^1$ is aryl or heteroaryl, wherein at least one of the two meta positions of each aryl and heteroaryl group is substituted with $R^5$;
$R^2$ is hydrogen, alkyl or cycloalkyl;
$R^3$ is cycloalkyl, aryl or heteroaryl, wherein at least one of the two ortho positions of each cycloalkyl, aryl and heteroaryl group is substituted with $R^6$;
$R^4$ is hydrogen, alkyl or cycloalkyl;
$R^5$ is hydrogen, cyano, trifluoromethyl, alkyl-$SO_2$—, amino-$SO_2$—, halogen, alkoxy, alkylcarbonyl or aminocarbonyl;
$R^6$ is hydrogen, halogen, cyano, nitro, trifluoromethyl, alkyl, alkoxy, hydroxy or alkoxycarbonyl; and
with the proviso that one of $R^5$ and $R^6$ is not hydrogen.

The compounds of formula I and their pharmaceutically acceptable salts are neuropeptide ligands, for example neuropeptide receptor antagonists and in particular, they are selective neuropeptides Y Y5 receptor antagonists. The compounds of formula I and their pharmaceutically acceptable salts and esters can be used in the prophylaxis or treatment of arthritis, cardiovascular diseases, diabetes, renal failure and particularly eating disorders and obesity.

In the present description the term "alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms Examples of straight-chain and branched $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl and ethyl and most preferred methyl.

The term "cycloalkyl", alone or in combination, signifies a cycloalkyl ring with 3 to 8 carbon atoms and preferably a cycloalkyl ring with 3 to 6 carbon atoms. Examples of $C_3$-$C_8$ cycloalkyl are cyclopropyl, methyl-cyclopropyl, dimethyl-cyclopropyl, cydobutyl, methyl-cyclobutyl, cyclopentyl, methyl-cyclopentyl, cyclohexyl, methyl-cyclohexyl, dimethyl-cyclohexyl, cycloheptyl and cyclooctyl, preferably cyclopropyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec. butoxy and tert.butoxy, 2-hydroxyethoxy, 2-methoxyethoxypreferably methoxy and ethoxy and most preferred methoxy.

The term "aryl", alone or in combination, signifies a phenyl or naphthyl group, preferably a phenyl group which optionally carries one or more substituents each independently selected from halogen, trifluoromethyl, amino, alkyl, alkoxy, alkylcarbonyl, cyano, carbamoyl, alkoxycarbamoyl, methylendioxy, carboxy, alkoxycarbonyl, aminocarbonyl, alkylaminocarbonyl, dialkylaminocarbonyl, hydroxy, nitro, alkyl-SO$_2$—, amino-SO$_2$—, and cycloalkyl. Preferred is phenyl or naphthyl, particularly phenyl optionally substituted with substituents independently selected from cyano, trifluoromethyl, alkyl-SO$_2$—, amino-SO$_2$—, halogen, alkoxy, hydroxy, amino, cycloalkyl, alkylcarbonyl, aminocarbonyl, nitro, alkyl and alkoxycarbonyl.

The term "aralkyl", alone or in combination, signifies an alkyl or cycloalkyl group as previously defined in which one hydrogen atom has been replaced by an aryl group as previously defined. Preferred are benzyl, benzyl substituted with hydroxy, alkoxy or halogen, preferably fluorine. Particularly preferred is benzyl.

The term "heteroaryl", alone or in combination, signifies aromatic 5- to 10-membered heterocycle which comprises one or more, preferably one or two, particularly preferred one hetero atom selected from nitrogen, oxygen and sulfur, wherein nitrogen is preferred. It can be substituted on one or more carbon atoms by a group selected from cyano, trifluoromethyl, alkyl-SO$_2$—, amino-SO$_2$—, halogen, alkoxy, hydroxy, amino, cycloalkyl, alkylcarbonyl, aminocarbonyl nitro, alkyl, and alkoxycarbonyl. Preferred heteroaryl cycles are pyridyl, pyrazinyl and thiophenyl optionally substituted by one or more, preferably one or two substituents independently selected from cyano, trifluoromethyl, alkyl-SO$_2$—, amino-SO$_2$—, halogen, alkoxy, alkylcarbonyl, aminocarbonyl, nitro, alkyl and alkoxycarbonyl.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substituents together forming a ring. Examples of amino include —NH$_2$, methylamino, ethylamino, dimethylamino, diethylamino, methyl-ethylamino, pyrrolidin-1-yl or piperidino etc., preferably amino, dimethylamino and diethylamino and particularly primary amino.

The term "halogen" signifies fluorine, chlorine, bromine or iodine and preferably fluorine, chlorine or bromine.

The term "carbonyl", alone or in combination signifies the —C(O)— group.

The term "nitro", alone or in combination signifies the —NO$_2$ group.

The term "cyano", alone or in combination signifies the group —CN.

The term "meta position" as used in the definition of substituent R$^1$ means that substituent R$^5$ is attached to the aryl or heteroaryl cycle in meta position to the atom of the aryl or heteroaryl cycle which is attached to the —NR$^2$— group. For example in case aryl means phenyl in the definition of R$^1$ the substituent(s) R$^5$ is (are) attached to the phenyl cycle according to the following formulae:

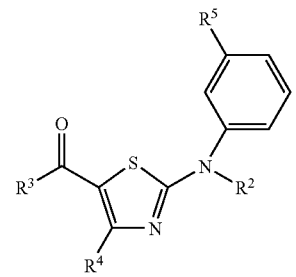

A

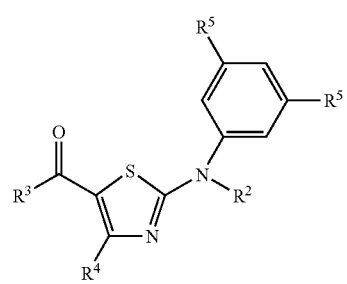

B

According to the definition of substituent R$^1$ the aryl or heteroaryl cycle is substituted by one or two R$^5$ substituents. In case two R$^5$ substituents are attached to the aryl or heteroaryl cycle the two R$^5$ substituents are the same or are different. Preferably, both R$^5$ substituents are the same. The R$^5$ substituents are independently selected from hydrogen, cyano, trifluoromethyl, alkyl-SO$_2$—, amino-SO$_2$—, halogen, alkoxy, alkylcarbonyl and aminocarbonyl.

The term "ortho position" as used in the definition of substituent R$^3$ means that substituent R$^6$ is attached to the cycloalkyl, aryl or heteroaryl cycle in ortho position to the atom of the cycloalkyl, aryl or heteroaryl which is attached to the carbonyl group. For example in case aryl means phenyl in the definition of R$^3$ the substituent(s) R$^6$ is (are) attached to the phenyl cycle according to the following formulae:

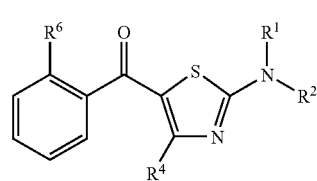

C

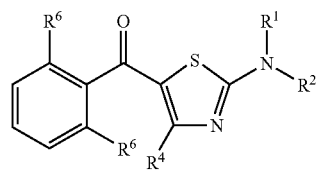

D

According to the definition of substituent R$^3$ the cycloalkyl, aryl or heteroaryl cycle can be substituted by one or two R$^6$ substituents. In case two R$^6$ substituents are attached to the cycloalkyl, aryl or heteroaryl cycle the two R$^6$ substituents can be the same or can be different. Preferably, both R$^6$ substituents are the same.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the hydrochloride salts.

The compounds of formula I can also be solvated, e.g. hydrated. The solvation can be effected in the course of the manufacturing process or can take place e.g. as a consequence of hygroscopic properties of an initially anhydrous compound of formula I (hydration). The term pharmaceutically acceptable salts also includes physiologically acceptable solvates.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention. For example, esters may be formed wherein aryl is substituted with carboxy, or wherein aryl, aralkyl or heteroaryl is substituted with hydroxy.

The term "lipase inhibitor" refers to compounds which are capable of inhibiting the action of lipases, for example gastric and pancreatic lipases. For example orlistat and lipstatin as described in U.S. Pat. No. 4,598,089 are potent inhibitor of lipases. Lipstatin is a natural product of microbial origin, and orlistat is the result of a hydrogenation of lipstatin. Other lipase inhibitors include a class of compound commonly referred to as panclicins. Panclicins are analogues of orlistat (Mutoh et al, 1994). The term "lipase inhibitor" refers also to polymer bound lipase inhibitors for example described in International Patent Application WO99/34786 (Geltex Pharmaceuticals Inc.). These polymers are characterized in that they have been substituted with one or more groups that inhibit lipases. The term "lipase inhibitor" also comprises pharmaceutically acceptable salts of these compounds. The term "lipase inhibitor" preferably refers to orlistat.

Orlistat is a known compound useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123. Additional processes for the preparation of orlistat are disclosed in European Patent Applications Publication Nos. 185,359, 189,577, 443,449, and 524,495.

Orlistat is preferably orally administered from 60 to 720 mg per day in divided doses two to three times per day. Preferred is wherein from 180 to 360 mg, most preferably 360 mg per day of a lipase inhibitor is administered to a subject, preferably in divided doses two or, particularly, three times per day. The subject is preferably an obese or overweight human, i.e. a human with a body mass index of 25 or greater. Generally, it is preferred that the lipase inhibitor be administered within about one or two hours of ingestion of a meal containing fat. Generally, for administering a lipase inhibitor as defined above it is preferred that treatment be administered to a human who has a strong family history of obesity and has obtained a body mass index of 25 or greater.

Orlistat can be administered to humans in conventional oral compositions, such as, tablets, coated tablets, hard and soft gelatin capsules, emulsions or suspensions. Examples of carriers which can be used for tablets, coated tablets, dragees and hard gelatin capsules are lactose, other sugars and sugar alcohols like sorbitol, mannitol, maltodextrin, or other fillers; surfactants like sodium lauryle sulfate, Brij 96, or Tween 80; disintegrants like sodium starch glycolate, maize starch or derivatives thereof; polymers like povidone, crospovidone; talc; stearic acid or its salts and the like. Suitable carriers for soft gelatin capsules are, for example, vegetable oils, waxes, fats, semi-solid and liquid polyols and the like. Moreover, the pharmaceutical preparations can contain preserving agents, solubilizers, stabilizing agents, wetting agents, emulsifying agents, sweetening agents, coloring agents, flavoring agents, salts for varying the osmotic pressure, buffers, coating agents and antioxidants. They can also contain still other therapeutically valuable substances. The formulations may conveniently be presented in unit dosage form and may be prepared by any methods known in the pharmaceutical art. Preferably, orlistat is administered according to the formulation shown in the Examples and in U.S. Pat. No. 6,004,996, respectively.

The compounds of formula I can contain several asymmetric centers and can be present in the form of optically pure enantiomers, mixtures of enantiomers such as, for example, racemates, optically pure diastereoisomers, mixtures of diastereo-isomers, diastereoisomeric racemates or mixtures of diastereoisomeric racemates.

Preferred are the compounds of formula I and pharmaceutically acceptable salts thereof, particularly the compounds of formula I.

Further preferred are compound of formula I, wherein $R^1$ is aryl or heteroaryl, wherein at least one of the two meta positions of each aryl and heteroaryl group is substituted with $R^5$;

$R^2$ is hydrogen, alkyl or cycloalkyl;

$R^3$ is cycloalkyl, aryl or heteroaryl, wherein at least one of the two ortho positions of each cycloalkyl, aryl and heteroaryl group is substituted with $R^6$;

$R^4$ is hydrogen, alkyl or cycloalkyl;

$R^5$ is cyano, trifluoromethyl, alkyl-$SO_2$—, amino-$SO_2$—, halogen, alkoxy, alkylcarbonyl or aminocarbonyl;

$R^6$ is halogen, cyano, nitro, trifluoromethyl, alkyl, alkoxy, hydroxy or alkoxycarbonyl;

and pharmaceutically acceptable salts and esters thereof.

Further preferred are the compounds of formula I, wherein $R^1$ is aryl or heteroaryl and, wherein one of the two meta positions of each aryl and heteroaryl group is substituted with $R^5$, wherein $R^5$ is defined as before.

Also preferred are the compounds of formula I, wherein $R^3$ is cycloalkyl, aryl or heteroaryl and wherein one of the two ortho positions of each cycloalkyl, aryl and heteroaryl group is substituted with $R^6$, wherein $R^6$ is defined as before.

Also preferred are compounds according to formula I, wherein $R^4$ is hydrogen or methyl. Particularly preferred are those compounds of formula I, wherein $R^4$ is hydrogen.

Other preferred compounds of formula I are those, wherein $R^2$ is hydrogen.

Further preferred compounds of formula I are those, wherein $R^3$ is cylohexyl, naphthyl, phenyl, pyridyl, pyrazinyl or thiophenyl, wherein at least one of the two ortho positions of each cylohexyl, naphthyl, phenyl, pyridyl, pyrazinyl and thiophenyl group is substituted with $R^6$, wherein $R^6$ is defined as before.

Another preferred embodiment of the present invention is the compounds according to formula I, wherein $R^3$ is phenyl or pyridyl and wherein at least one of the two ortho positions of each phenyl and pyridyl group is substituted with $R^6$, wherein $R^6$ is defined as before.

Also preferred are compounds according to formula I, wherein $R^1$ is phenyl or pyridyl and, wherein at least one of the two meta positions of each phenyl or pyridyl group is substituted with $R^5$ and, wherein $R^5$ is defined as before.

Another preferred embodiment of the present invention is the compounds of formula I, wherein $R^1$ is phenyl or pyridyl and wherein one of the two meta positions of each phenyl or pyridyl group is substituted with cyano, trifluoromethyl, alkyl-$SO_2$—, amino-$SO_2$—, halogen, alkoxy, alkylcarbonyl or aminocarbonyl.

Also preferred are compounds of formula I, wherein $R^5$ is cyano, trifluoromethyl, alkyl-$SO_2$—, amino-$SO_2$—, halogen, alkoxy, alkylcarbonyl or aminocarbonyl.

Another preferred aspect of the present invention are the compounds of formula I, wherein $R^5$ is cyano, trifluoromethyl, alkyl-$SO_2$—, amino-$SO_2$— or alkylcarbonyl.

Further preferred are the compounds of formula I, wherein $R^5$ is cyano, trifluoromethyl, methyl-$SO_2$—, $NH_2$—$SO_2$— or methylcarbonyl.

Also preferred are the compounds of formula I, wherein $R^6$ is halogen, cyano, nitro, trifluoromethyl, alkyl, alkoxy, hydroxy or alkoxycarbonyl.

Further preferred are the compounds of formula I, wherein $R^6$ is halogen, trifluoromethyl or alkyl.

Examples of preferred compounds of formula (I) are:
1. 3-[5-(Naphthalene-2-carbonyl)-thiazol-2-ylamino]-benzonitrile;
2. 3-(5-Benzoyl-thiazol-2-ylamino)-benzonitrile;
3. 3-[5-(4-Methyl-benzoyl)-thiazol-2-ylamino]-benzonitrile;
4. [2-(3-Methanesulfonyl-phenylamino)-thiazol-5-yl]-phenyl-methanone;
5. [2-(3-Methoxy-phenylamino)-thiazol-5-yl]-phenyl-methanone;
6. Phenyl-[2-(3-trifluoromethyl-phenylamino)-thiazol-5-yl]-methanone;
7. 3-[5-(3-Methoxy-benzoyl)-thiazol-2-ylamino]-benzonitrile;
8. 3-[5-(4-Fluoro-benzoyl)-thiazol-2-ylamino]-benzonitrile;
9. 3-[5-(4-Chloro-benzoyl)-thiazol-2-ylamino]-benzonitrile;
10. [2-(3,5-Dichloro-phenylamino)-thiazol-5-yl]-(2-fluoro-phenyl)-methanone;
11. (2-Chloro-phenyl)-[2-(3,5-dichloro-phenylamino)-thiazol-5-yl]-methanone;
12. 3-[5-(4-Bromo-benzoyl)-thiazol-2-ylamino]-benzonitrile;
13. 3-[5-(3-Chloro-benzoyl)-thiazol-2-ylamino]-benzonitrile;
14. 3-[5-(2-Fluoro-benzoyl)-thiazol-2-ylamino]-benzonitrile;
15. 3-[5-(3-Fluoro-benzoyl)-thiazol-2-ylamino]-benzonitrile;
16. 3-[5-(2-Methoxy-benzoyl)-thiazol-2-ylamino]-benzonitrile;
17. 3-[5-(3-Trifluoromethyl-benzoyl)-thiazol-2-ylamino]-benzonitrile;
18. 3-[5-(2-Chloro-benzoyl)-thiazol-2-ylamino]-benzonitrile;
19. 3-[5-(3-Bromo-benzoyl)-thiazol-2-ylamino]-benzonitrile;
20. [2-(4-Chloro-phenylamino)-thiazol-5-yl]-(2-fluoro-phenyl)-methanone;
21. (2-Chloro-phenyl)-[2-(4-chloro-phenylamino)-thiazol-5-yl]-methanone;
22. p-Tolyl-[2-(3-trifluoromethyl-phenylamino)-thiazol-5-yl]-methanone;
23. (4-Fluoro-phenyl)-[2-(3-trifluoromethyl-phenylamino)-thiazol-5-yl]-methanone;
24. (3-Methoxy-phenyl)-[2-(3-trifluoromethyl-phenylamino)-thiazol-5-yl]-methanone;
25. (3-Chloro-phenyl)-[2-(3-trifluoromethyl-phenylamino)-thiazol-5-yl]-methanone;
26. (2-Fluoro-phenyl)-[2-(3-trifluoromethyl-phenylamino)-thiazol-5-yl]-methanone;
27. (3-Fluoro-phenyl)-[2-(3-trifluoromethyl-phenylamino)-thiazol-5-yl]-methanone;
28. (2-Methoxy-phenyl)-[2-(3-trifluoromethyl-phenylamino)-thiazol-5-yl]-methanone;
29. (2-Chloro-phenyl)-[2-(3-trifluoromethyl-phenylamino)-thiazol-5-yl]-methanone;
30. (3-Bromo-phenyl)-[2-(3-trifluoromethyl-phenylamino)-thiazol-5-yl]-methanone;
31. [2-(Pyridin-4-ylamino)-thiazol-5-yl]-o-tolyl-methanone;
32. (2,4-Dichloro-phenyl)-[2-(pyridin-4-ylamino)-thiazol-5-yl]-methanone;
33. (2,4-Dimethyl-phenyl)-[2-(pyridin-4-ylamino)-thiazol-5-yl]-methanone;
34. (2-Nitro-phenyl)-[2-(pyridin-4-ylamino)-thiazol-5-yl]-methanone;
35. 3-[5-(Pyridine-2-carbonyl)-thiazol-2-ylamino]-benzonitrile;
36. 3-[5-(Pyridine-3-carbonyl)-thiazol-2-ylamino]-benzonitrile;
37. 3-[5-(Pyridine-4-carbonyl)-thiazol-2-ylamino]-benzonitrile;
38. 3-[5-(2-Methyl-benzoyl)-thiazol-2-ylamino]-benzonitrile;
39. 3-(5-Cyclohexanecarbonyl-thiazol-2-ylamino)-benzonitrile;
40. 3-[5-(2,4-Dichloro-benzoyl)-thiazol-2-ylamino]-benzonitrile;
41. 3-[5-(2,4-Dimethyl-benzoyl)-thiazol-2-ylamino]-benzonitrile;
42. 3-[5-(2-Nitro-benzoyl)-thiazol-2-ylamino]-benzonitrile;
43. (2-Fluoro-phenyl)-[2-(3-methoxy-phenylamino)-thiazol-5-yl]-methanone;

44. [2-(3-Methoxy-phenylamino)-thiazol-5-yl]-o-tolyl-methanone;
45. (2,4-Dimethyl-phenyl)-[2-(3-methoxy-phenylamino)-thiazol-5-yl]-methanone;
46. [2-(3-Methoxy-phenylamino)-thiazol-5-yl]-(2-nitro-phenyl)-methanone;
47. Pyridin-4-yl-[2-(3-trifluoromethyl-phenylamino)-thiazol-5-yl]-methanone;
48. o-Tolyl-[2-(3-trifluoromethyl-phenylamino)-thiazol-5-yl]-methanone;
49. Cyclohexyl-[2-(3-trifluoromethyl-phenylamino)-thiazol-5-yl]-methanone;
50. (2,4-Dichloro-phenyl)-[2-(3-trifluoromethyl-phenylamino)-thiazol-5-yl]-methanone;
51. (2,4-Dimethyl-phenyl)-[2-(3-trifluoromethyl-phenylamino)-thiazol-5-yl]-methanone;
52. (2-Nitro-phenyl)-[2-(3-trifluoromethyl-phenylamino)-thiazol-5-yl]-methanone;
53. (2-Fluoro-phenyl)-[2-(3-fluoro-phenylamino)-thiazol-5-yl]-methanone;
54. [2-(3-Fluoro-phenylamino)-thiazol-5-yl]-o-tolyl-methanone;
55. (2-Chloro-phenyl)-[2-(3-fluoro-phenylamino)-thiazol-5-yl]-methanone;
56. [2-(3-Bromo-phenylamino)-thiazol-5-yl]-phenyl-methanone;
57. [2-(3-Bromo-phenylamino)-thiazol-5-yl]-o-tolyl-methanone;
58. [2-(3-Bromo-phenylamino)-thiazol-5-yl]-(2-chloro-phenyl)-methanone;
59. [2-(3-Bromo-phenylamino)-thiazol-5-yl]-(2,4-dimethyl-phenyl)-methanone;
60. 1-{3-[5-(2-Fluoro-benzoyl)-thiazol-2-ylamino]-phenyl}-ethanone;
61. 1-{3-[5-(2-Methyl-benzoyl)-thiazol-2-ylamino]-phenyl}-ethanone;
62. 1-{3-[5-(2-Chloro-benzoyl)-thiazol-2-ylamino]-phenyl}-ethanone;
63. 1-{3-[5-(2,4-Dimethyl-benzoyl)-thiazol-2-ylamino]-phenyl}-ethanone;
64. (2-Fluoro-phenyl)-[2-(pyridin-3-ylamino)-thiazol-5-yl]-methanone;
65. [2-(Pyridin-3-ylamino)-thiazol-5-yl]-o-tolyl-methanone;
66. (2-Chloro-phenyl)-[2-(pyridin-3-ylamino)-thiazol-5-yl]-methanone;
67. 3-[5-(3-Methyl-pyrazine-2-carbonyl)-thiazol-2-ylamino]-benzonitrile;
68. 3-[5-(3-Ethyl-pyrazine-2-carbonyl)-thiazol-2-ylamino]-benzonitrile;
69. 3-[5-(3-Methyl-thiophene-2-carbonyl)-thiazol-2-ylamino]-benzonitrile;
70. 3-[5-(2-Ethyl-benzoyl)-thiazol-2-ylamino]-benzonitrile;
71. 3-[5-(2-Trifluoromethyl-benzoyl)-thiazol-2-ylamino]-benzonitrile;
72. 3-[5-(3-Methyl-pyridine-2-carbonyl)-thiazol-2-ylamino]-benzonitrile;
73. 3-[5-(2-Methyl-pyridine-3-carbonyl)-thiazol-2-ylamino]-benzonitrile;
74. 3-[5-(2,5-Dimethyl-thiophene-3-carbonyl)-thiazol-2-ylamino]-benzonitrile;
75. (3-Methyl-thiophen-2-yl)-[2-(3-trifluoromethyl-phenylamino)-thiazol-5-yl]-methanone;
76. (2-Ethyl-phenyl)-[2-(3-trifluoromethyl-phenylamino)-thiazol-5-yl]-methanone;
77. (2-Trifluoromethyl-phenyl)-[2-(3-trifluoromethyl-phenylamino)-thiazol-5-yl]-methanone;
78. (3-Methyl-pyridin-2-yl)-[2-(3-trifluoromethyl-phenylamino)-thiazol-5-yl]-methanone;
79. (2,5-Dimethyl-thiophen-3-yl)-[2-(3-trifluoromethyl-phenylamino)-thiazol-5-yl]-methanone;
80. o-Tolyl-(2-m-tolylamino-thiazol-5-yl)-methanone;
81. (2-Ethyl-phenyl)-(2-m-tolylamino-thiazol-5-yl)-methanone;
82. (2-m-Tolylamino-thiazol-5-yl)-(2-trifluoromethyl-phenyl)-methanone;
83. (2-Fluoro-phenyl)-(2-m-tolylamino-thiazol-5-yl)-methanone;
84. (2-Chloro-phenyl)-(2-m-tolylamino-thiazol-5-yl)-methanone;
85. (2-Methoxy-phenyl)-(2-m-tolylamino-thiazol-5-yl)-methanone;
86. (2,5-Dimethyl-thiophen-3-yl)-(2-m-tolylamino-thiazol-5-yl)-methanone;
87. [2-(3-Methanesulfonyl-phenylamino)-thiazol-5-yl]-o-tolyl-methanone;
88. (2-Ethyl-phenyl)-[2-(3-methanesulfonyl-phenylamino)-thiazol-5-yl]-methanone;
89. [2-(3-Methanesulfonyl-phenylamino)-thiazol-5-yl]-(2-trifluoromethyl-phenyl)-methanone;
90. (2-Chloro-phenyl)-[2-(3-methanesulfonyl-phenylamino)-thiazol-5-yl]-methanone;
91. [2-(3-Methanesulfonyl-phenylamino)-thiazol-5-yl]-(4-methyl-pyridin-3-yl)-methanone;
92. (2,5-Dimethyl-thiophen-3-yl)-[2-(3-methanesulfonyl-phenylamino)-thiazol-5-yl]-methanone;
93. 4-[5-(2-Ethyl-benzoyl)-thiazol-2-ylamino]-pyridine-2-carbonitrile;
94. 4-[5-(3-Methyl-pyridine-2-carbonyl)-thiazol-2-ylamino]-pyridine-2-carbonitrile;
95. 4-[5-(2-Methyl-benzoyl)-thiazol-2-ylamino]-pyridine-2-carbonitrile;
96. 4-[5-(2-Chloro-benzoyl)-thiazol-2-ylamino]-pyridine-2-carbonitrile;
97. 4-[5-(2-Fluoro-benzoyl)-thiazol-2-ylamino]-pyridine-2-carbonitrile;
98. 3-[5-(2-Methyl-benzoyl)-thiazol-2-ylamino]-benzenesulfonamide;
99. 3-[5-(2-Ethyl-benzoyl)-thiazol-2-ylamino]-benzenesulfonamide;
100. 3-[5-(4-Hydroxy-2-methyl-benzoyl)-thiazol-2-ylamino]-benzenesulfonamide;
101. 3-[5-(2-Trifluoromethyl-benzoyl)-thiazol-2-ylamino]-benzenesulfonamide;
102. 3-[5-(2-Fluoro-benzoyl)-thiazol-2-ylamino]-benzenesulfonamide;
103. 3-[5-(2-Chloro-benzoyl)-thiazol-2-ylamino]-benzenesulfonamide;
104. 3-[5-(2-Methoxy-benzoyl)-thiazol-2-ylamino]-benzenesulfonamide;
105. 3-[5-(3-Fluoro-benzoyl)-thiazol-2-ylamino]-benzenesulfonamide;
106. 3-[5-(3-Chloro-benzoyl)-thiazol-2-ylamino]-benzenesulfonamide;
107. 3-[5-(4-Methyl-pyridine-3-carbonyl)-thiazol-2-ylamino]-benzenesulfonamide;
108. 3-[5-(3-Methyl-pyridine-2-carbonyl)-thiazol-2-ylamino]-benzenesulfonamide;
109. 3-[5-(3-Ethyl-pyrazine-2-carbonyl)-thiazol-2-ylamino]-benzenesulfonamide;
110. 3-[5-(3-Methyl-thiophene-2-carbonyl)-thiazol-2-ylamino]-benzenesulfonamide;
111. 3-[4-Methyl-5-(2-trifluoromethyl-benzoyl)-thiazol-2-ylamino]-benzonitrile and 112. Phenyl-(2-m-tolylamino-thiazol-5-yl)-methanone.

Examples of particularly preferred compounds of formula (I) are:

3-[5-(2-Fluoro-benzoyl)-thiazol-2-ylamino]-benzonitrile;
3-[5-(2-Chloro-benzoyl)-thiazol-2-ylamino]-benzonitrile;
(2-Chloro-phenyl)-[2-(3-trifluoromethyl-phenylamino)-thiazol-5-yl]-methanone;
3-[5-(2-Methyl-benzoyl)-thiazol-2-ylamino]-benzonitrile;
o-Tolyl-[2-(3-trifluoromethyl-phenylamino)-thiazol-5-yl]-methanone;
1-{3-[5-(2-Methyl-benzoyl)-thiazol-2-ylamino]-phenyl}-ethanone;
3-[5-(2-Ethyl-benzoyl)-thiazol-2-ylamino]-benzonitrile;
3-[5-(2-Trifluoromethyl-benzoyl)-thiazol-2-ylamino]-benzonitrile;
3-[5-(3-Methyl-pyridine-2-carbonyl)-thiazol-2-ylamino]-benzonitrile;
[2-(3-Methanesulfonyl-phenylamino)-thiazol-5-yl]-o-tolyl-methanone;
(2-Ethyl-phenyl)-[2-(3-methanesulfonyl-phenylamino)-thiazol-5-yl]-methanone;
4-[5-(2-Ethyl-benzoyl)-thiazol-2-ylamino]-pyridine-2-carbonitrile;
4-[5-(2-Methyl-benzoyl)-thiazol-2-ylamino]-pyridine-2-carbonitrile;
3-[5-(2-Ethyl-benzoyl)-thiazol-2-ylamino]-benzenesulfonamide; and
3-[5-(2-Trifluoromethyl-benzoyl)-thiazol-2-ylamino]-benzenesulfonamide.

The preparation of compounds of formula I of the present invention may be carried out in sequential or convergent synthetic routes. Syntheses of the invention are shown in the following Schemes. The skills required for carrying out the reaction and purification of the resulting products are known to those in the art. The substituents and indices used in the following description of the processes have the significance given above unless indicated to the contrary.

Compounds of general formula IA ($R^4$=H) can be prepared according to scheme 1 as follows:

a) Thioureas IB, either commercially available or accessible via various procedures described in literature, are conveniently reacted with N,N-dimethylformamide dimethyl acetal in the presence or the absence of a solvent. There is no particular restriction on the nature of the solvent to be employed, provided that it has no adverse effect on the reaction or the reagents involved and that it can dissolve the reagents, at least to some extent. Examples for suitable solvents include: DMF and dioxane and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the Dimethylaminomethylene-thioureido derivatives IC. For reaction conditions described in literature affecting such a reaction see for example: Heterocycles 11, 313-318; 1978.

b) Dimethylaminomethylene-thioureido derivatives IC can be converted to thiazole derivatives IA ($R^4$=H) by reaction of IA with α-bromoketones ID (a known compound or compound prepared by known methods. The source for α-bromoketones employed is indicated as appropriate) in a solvent such as ethanol, and the like, in the presence or the absence of a base. There is no particular restriction on the nature of the solvent to be employed, provided that it has no adverse effect on the reaction or the reagents involved and that it can dissolve the reagents, at least to some extent. Examples for suitable solvents include: dichloromethane, chloroform, or dioxane, methanol, ethanol and the like. There is no particular restriction on the nature of the base used in this stage, and any base commonly used in this type of reaction may equally be employed here. Examples of such bases include triethylamine and diisopropylethylamine, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the thiazole derivatives IA. For reaction conditions described in literature affecting such a reaction see for example: J. Heterocycl. Chem., 16 (7), 1377-83; 1979. The resulting compound of formula IA ($R^4$=H, $R^2$=H) is a compound of the present invention and may be the desired product; alternatively it may be subjected to consecutive reactions like removal of a protecting group by methods described widely in literature to yield the desired thiazole derivatives IA. However, the resulting compound of formula IA is a compound of the present invention and may be the desired product; alternatively it may be subjected to consecutive reactions. Introduction of $R^2$=alkyl or cycloalky (in the case $R^2$=H) in IA can be affected by reductive amination of IA with the respective aldehyde under reducing conditions in a solvent. There is no particular restriction on the nature of the solvent to be employed, provided that it has no adverse effect on the reaction or the reagents involved and that it can dissolve the reagents, at least to some extent. Examples for suitable solvents include: dichloromethane, chloroform, dioxane, THF, and the like. There is no particular restriction on the nature of the reducing agent used in this stage, and any reducing agent commonly used in this type of reaction may equally be employed here. Examples of such reducing agents include $NaBH_4$, $NaCNBH_3$, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the desired thiazole derivatives IA ($R^2$=alkyl or cycloalkyl). For reaction conditions described in literature affecting a reductive amination see for example: Reductive amination in: A Guide to Functional Group Preparations, 2nd Edition, Richard C. Larock. John Wiley & Sons, New York, N.Y. 1999. The resulting compound of formula IA ($R^2$=alkyl or cycloalkyl) is a compound of the present invention and may be the desired product; alternatively it may be subjected to consecutive reactions like removal of a protecting group by methods described widely in literature to yield the desired thiazole derivatives IA.

Scheme 1

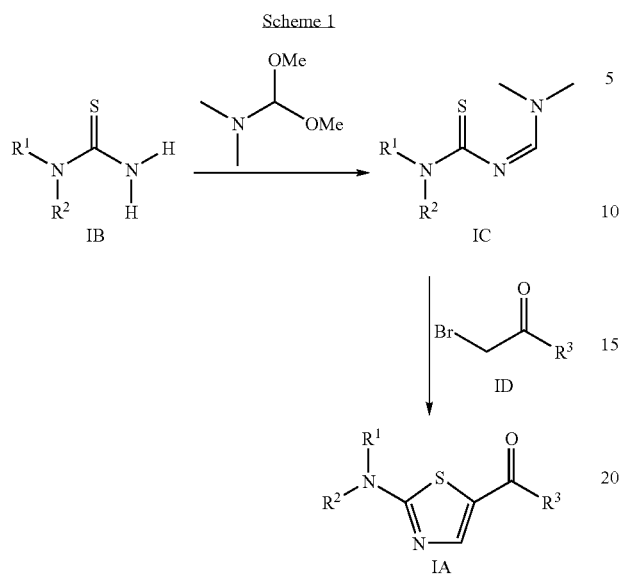

Compounds of general formula IA ($R^4$=alkyl or cycloalkyl) can be prepared according to scheme 2 as follows:

a) Thioisocyanates IIA are commercially available or can be prepared from suitable starting materials according to methods known in the art. The elaboration of the thioisocyanate-moiety like in IIA to a thioureido-moiety like in IIC can be affected by methods described in literature. For example compounds of the general formula IIA are condensed with an amidine of general formula IIB or their salts ($R^4$=alkyl, cycloakly), a known compound or compound prepared by known methods, in a solvent such as THF, or the like, and a base, such as NaOH, or the like. There is no particular restriction on the nature of the solvent to be employed, provided that it has no adverse effect on the reaction or the reagents involved and that it can dissolve the reagents, at least to some extent. Examples for suitable solvents include: dichloromethane, chloroform, dioxane, THF and the like. There is no particular restriction on the nature of the base used in this stage, and any base commonly used in this type of reaction may equally be employed here. Examples of such bases include NaOHaq., KOHaq, NEt$_3$, and the like. The reaction can take place over a wide range of temperatures, and the precise reaction temperature is not critical to the invention. We find it convenient to carry out the reaction from 0° C. to heating to reflux temperature of the solvent. The time required for the reaction may also vary widely, depending on many factors, notably the reaction temperature and the nature of the reagents. However, a period of from 0.5 h to several days will usually suffice to yield the thioureido derivatives IIC. For reaction conditions described in literature affecting such a reaction see for example: C. R. Seances Acad. Sci., Ser. 2, 294 (19), 1183-6; 1982. Dimethylaminomethylene-thioureido derivatives IIC can be converted to thiazole derivatives IID ($R^4$=alkyl, cycloalkyl) by reaction of IIC with α-bromoketones ID (a known compound or compound prepared by known methods. The source for α-bromoketones employed is indicated as appropriate) in a solvent such as ethanol, and the like, in the presence or the absence of a base. There is no particular restriction on the nature of the solvent to be employed, provided that it has no adverse effect on the reaction or the reagents involved and that it can dissolve the reagents, at least to some extent. Examples for suitable solvents include: dichloromethane, chloroform, DMF, dioxane, methanol, ethanol and the like. There is no particular restriction on the nature of the base used in this stage, and any base commonly used in this type of reaction may equally be employed here. Examples of such bases include triethylamine and diisopropylethylamine, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the thiazole derivatives IID. For reaction conditions described in literature affecting such a reaction see for example: Org. Chem., 65 (21), 7244-7247; 2000. The resulting compound of formula IID ($R^4$=alkyl or cycloalkyl, $R^2$=H) is a compound of the present invention and may be the desired product; alternatively it may be subjected to consecutive reactions like removal of a protecting group by methods described widely in literature to yield the desired thiazole derivatives IA ($R^4$=alkyl or cycloalkyl, $R^2$=H). However, the resulting compound of formula IID is a compound of the present invention and may be the desired product; alternatively it may be subjected to consecutive reactions. Introduction of $R^2$=alkyl or cycloalky can be affected by reductive amination of IID with the respective aldehyde under reducing conditions in a solvent. There is no particular restriction on the nature of the solvent to be employed, provided that it has no adverse effect on the reaction or the reagents involved and that it can dissolve the reagents, at least to some extent. Examples for suitable solvents include: dichloromethane, chloroform, dioxane, THF, and the like. There is no particular restriction on the nature of the reducing agent used in this stage, and any reducing agent commonly used in this type of reaction may equally be employed here. Examples of such reducing agents include NaBH$_4$, NaCNBH$_3$, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the thiazole derivatives IA ($R^4$=alkyl or cycloalkyl $R^2$=alkyl or cycloalkyl). For reaction conditions described in literature affecting a reductive amination see for example: Reductive amination in: A Guide to Functional Group Preparations, 2nd Edition, Richard C. Larock. John Wiley & Sons, New York, N.Y. 1999. The resulting compound of formula IA ($R^4$=alkyl or cycloalkyl, $R^2$=alkyl or cycloalkyl) is a compound of the present invention and may be the desired product; alternatively it may be subjected to consecutive reactions like removal of a protecting group by methods described widely in literature to yield the desired thiazole derivatives IA ($R^4$=alkyl or cycloalkyl, $R^2$=alkyl or cycloalkyl).

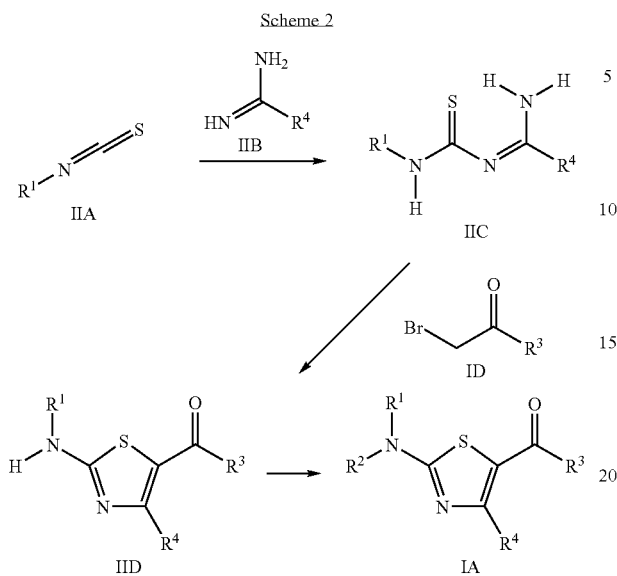

The conversion of a compound of formula I into a pharmaceutically acceptable salt can be carried out by treatment of such a compound with an inorganic acid, for example a hydrohalic acid, such as, for example, hydrochloric acid or hydrobromic acid, sulfuric acid, nitric acid, phosphoric acid etc., or with an organic acid, such as, for example, acetic acid, citric acid, maleic acid, fumaric acid, tartaric acid, methanesulfonic acid or p-toluenesulfonic acid. The corresponding carboxylate salts can also be prepared from the compounds of formula I by treatment with physiologically compatible bases.

The conversion of compounds of formula I into pharmaceutically acceptable esters or amides can be carried out e.g. by treatment of suited amino or hydroxyl groups present in the molecules with an carboxylic acid such as acetic acid, with a condensating reagent such as benzotriazol-1-yloxytris(dimethylamino)phosphonium hexafluorophosphate (BOP) or N,N-dicylohexylcarbodiimide (DCCI) to produce the carboxylic ester or carboxylic amide.

A preferred process for the preparation of a compound of formula I comprises one of the following reactions
a) reaction of a compound according to formula IIC in the presence of a compound according to formula ID in order to obtain a compound of formula I

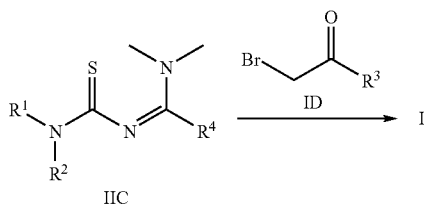

wherein $R^1$ to $R^4$ are defined as before;
b) reaction of a compound according to formula IID in the presence of $R^2$—CHO in order to obtain a compound of formula I wherein $R^1$, $R^3$ and $R^4$ are defined as before and $R^2$ means alkyl or cycloalkyl. Preferred is the above reaction under reducing conditions, particularly in the presence of an reducing agent such as $NaBH_4$ or $NaCNBH_3$.

Preferred intermediates are:
1-Dimethylaminomethylene-3-(3-methanesulfonyl-phenyl)-thiourea;
1-(2-Cyano-pyridin-4-yl)-3-dimethylaminomethylene-thiourea;
1-Dimethylaminomethylene-3-(3-cyano-phenyl)-thiourea;
1-Dimethylaminomethylene-3-pyridin-3-yl-thiourea;
1-Dimethylaminomethylene-3-pyridin-4-yl-thiourea;
1-Dimethylaminomethylene-3-(3-bromo-phenyl)-thiourea;
1-Dimethylaminomethylene-3-(3-acetyl-phenyl)-thiourea;
1-Dimethylaminomethylene-3-(3-acetyl-phenyl)-thiourea; and
3-Thioureido-benzenesulfonamide The compounds of formula I described above for use as therapeutically active substances are a further object of the invention.

Also an object of the invention are compounds described above for the production of medicaments for the prophylaxis and therapy of illnesses which are caused by disorders associated with the NPY receptor, particularly for the production of medicaments for the prophylaxis and therapy of arthritis, cardiovascular diseases, diabetes, renal failure and particularly eating disorders and obesity.

Likewise an object of the invention are pharmaceutical compositions containing a compound of formula I described above and a therapeutically inert carrier.

An object of the invention is also the use of the compounds described above for the production of medicaments, particularly for the treatment and prophylaxis of arthritis, cardiovascular diseases, diabetes, renal failure and particularly eating disorders and obesity.

A further object of the invention comprises compounds which are manufactured according to one of the described processes.

A further object of the invention is a method for the treatment and prophylaxis of arthritis, cardiovascular diseases, diabetes, renal failure and particularly eating disorders and obesity whereby an effective amount of a compound described above is administered.

According to a further aspect of the invention there is provided a method of treatment of obesity in a human in need of such treatment which comprises administration to the human a therapeutically effective amount of a compound according to formula I and a therapeutically effective amount of a lipase inhibitor, particularly preferred, wherein the lipase inhibitor is orlistat. Also subject of the present invention is the mentioned method, wherein the administration is simultaneous, separate or sequential.

A further preferred embodiment of the present invention is the use of a compound of the formula I in the manufacture of a medicament for the treatment and prevention of obesity in a patient who is also receiving treatment with a lipase inhibitor, particularly preferred, wherein the lipase inhibitor is orlistat.

Also an object of the invention are compounds described above for the production of medicaments for the prophylaxis and therapy of alcoholism.

A further object of the invention is a method for the treatment and prophylaxis of alcoholism.

ASSAY PROCEDURES

Cloning of Mouse NPY5 Receptor cDNAs

The full-length cDNA encoding the mouse NPY5 (mNPY5) receptor was amplified from mouse brain cDNA using specific primers, designed based on the published sequence, and Pfu DNA-Polymerase. The amplification product was subcloned into the mammalian expression vector pcDNA3 using Eco RI and XhoI restriction sites. Positive clones were sequenced and one clone, encoding the published sequence was selected for generation of stable cell clones. The sequence is published in Borowsky B., et al., "Molecular Biology and Pharmacology of Multiple NPY Y5 Receptor Species Homologs", Regul. Pept. 75-76:45-53 (1998).

Stable Transfection

Human embryonic kidney 293 (HEK293) cells were transfected with 10 μg mNPY5 DNA using the lipofectamine reagent. Two days after transfection, geneticin selection (1 mg/ml) was initiated and several stable clones were isolated. One clone was further used for pharmacological characterization.

Radioligand Competition Binding

Human embryonic kidney 293 cells (HEK293), expressing recombinant mouse NPY5-receptor (mNPY5) were broken by three freeze/thawing cycles in hypotonic Tris buffer (5 mM, pH 7.4, 1 mM $MgCl_2$), homogenized and centrifuged at 72,000×g for 15 min. The pellet was washed twice with 75 mM Tris buffer, pH 7.4, containing 25 mM $MgCl_2$ and 250 mM sucrose, 0.1 mM phenylmethylsulfonylfluoride and 0.1 mM 1,10-pheneanthrolin, resuspended in the same buffer and stored in aliquots at −80° C. Protein was determined according to the method of Lowry using bovine serum albumine (BSA) as a standard.

Radioligand competition binding assays were performed in 250 μl 25 mM Hepes buffer (pH 7.4, 2.5 mM $CaCl_2$, 1 mM $MgCl_2$, 1% bovine serum albumine, and 0.01% $NaN_3$ containing 5 μg protein, 100 pM [$^{125}$I]labeled peptide YY (PYY) and 10 μL DMSO containing increasing amounts of unlabelled test compounds. After incubation for 1 h at 22° C., bound and free ligand are separated by filtration over glass fibre filters. Non specific binding is assessed in the presence of 1 μM unlabelled PYY. Specific binding is defined as the difference between total binding and non specific binding. $IC_{50}$ values are defined as the concentration of antagonist that displaces 50% of the binding of [$^{125}$I] labeled neuropeptide Y. It is determined by linear regression analysis after logit/log transformation of the binding data.

Results obtained in the foregoing test using representative compounds of the invention as the test compounds are shown in the following table:

| Compound | NPY5-R (mouse) $IC_{50}$ (nM) |
|---|---|
| (2-Chloro-phenyl)-[2-(3-trifluoromethyl-phenylamino)-thiazol-5-yl]-methanone (Example 29) | 8 |
| 3-[5-(4-Fluoro-benzoyl)-thiazol-2-ylamino]-benzonitrile (Example 8) | 66 |
| 1-{3-[5-(2-Methyl-benzoyl)-thiazol-2-ylamino]-phenyl}-ethanone (Example 61) | 86 |

The compounds as described above have $IC_{50}$ values below 1000 nM; preferred compounds have $IC_{50}$ values below 100 nM, particularly below 10 nM. Most preferred compounds have $IC_{50}$ values below 2 nM. These results have been obtained by using the foregoing test.

The compounds of formula I and their pharmaceutically acceptable salts and esters can be used as medicaments (e.g. in the form of pharmaceutical preparations). The pharmaceutical preparations can be administered internally, such as orally (e.g. in the form of tablets, coated tablets, dragees, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula I and their pharmaceutically acceptable salts and esters can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc. Suitable adjuvants for the production of solutions and syrups are, for example, water, polyols, saccharose, invert sugar, glucose, etc. Suitable adjuvants for injection solutions are, for example, water, alcohols, polyols, glycerol, vegetable oils, etc. Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

In accordance with the invention the compounds of formula I and their pharmaceutically acceptable salts can be used for the prophylaxis and treatment of arthritis, cardiovascular diseases, diabetes, renal failure and particularly eating disorders and obesity. The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given above can be exceeded when this is shown to be indicated. The invention is illustrated hereinafter by Examples, which have no limiting character.

EXAMPLES

Example A

1-Dimethylaminomethylene-3-(3-methanesulfonyl-phenyl)-thiourea

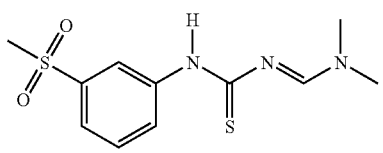

To a solution of 7.47 g (36 mmol) 3-Methylsulfonyl aniline hydrochloride and 6.15 ml diisopropylethylamine in 75 ml THF was added 5.87 g (36 mmol) benzoyl isothiocyanate dropwise and allowed to stir at room temperature for 1 h. The volatiles were removed under reduced pressure and the residue was treated with diethyl ether. The precipitate was filtered off, dried and dissolved in 100 ml THF and 130 ml methanol. 18 g (130 mmol) potassium carbonate in 45 ml water was added and the mixture was stirred for 24 h at room temperature. The reaction mixture was concentrated and diluted with water. The precipitate was filtered off, washed with diethyl ether/ethanol and dried. The crude solid was dissolved in 50 ml dimethylformamide dimethyl acteal and heated for 3 h to 90° C. The precipitate was filtered off, washed with THF and dried to obtain 9.3 g (90%) of the title compound as white solid.

1-H-NMR (250 MHz-DMSO-d6): δ=10.75 (s, br, 1H, NH), 8.78 (s, 1H, H-2), 8.57 (s, br, 1H, H-4), 7.72 (s, br, 1H, H-6), 7.53 (m, 2H, H-5/N=CH), 3.23 (s, 3H, $CH_3$), 3.17 (s, 3H, $OCH_3$), 3.09 (s, 3H, $OCH_3$).

MS (m/e): 286.2 (M+H, 100%)

Example B (2-Fluoro-phenyl)-[2-(3-methanesulfonyl-phenylamino)-thiazol-5-yl]-methanone

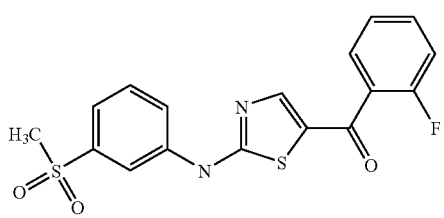

To a solution of 37 mg (0.13 mmol) 1-Dimethylaminomethylene-3-(3-methanesulfonyl-phenyl)-thiourea in 0.33 ml DMF was added 28 mg (0.13 mmol) 2-Fluorophenacyl bromide and the mixture was allowed to stir at room temperature for 16 h. 17 mg (0.13 mmol) diisopropylethylamine was added and the mixture was subjected to preparative HPLC separation on reversed phase eluting with an acetonitrile/water gradient to yield 38.5 mg (79%) of the title compound after evaporation of the product fractions.

1-H-NMR (500 MHz-DMSO): δ=8.31 (s, br, 1H, H-2), 7.88 (s, br, 1H, H-4), 7.78 (s, br, 1H, H-6), 7.63 (m, 4H, H-5/H-3'/H-6', thiazole-H), 7.37 (m, 2H, H-4'/H-5'), 3.37 (s, 3H, $CH_3$).

MS (m/e): 377.4 (M+H, 100%)

Example C 1-(2-Cyano-pyridin-4-yl)-3-dimethylaminomethylene-thiourea

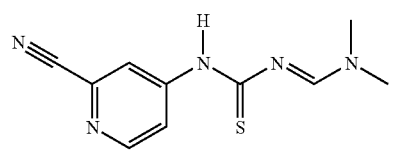

The title compound, MS (m/e): 234.2 (M+H, 100%), was synthesised according to the procedure in Example 1 from 2-Cyano-pyridin-4-yl-amine.

Example D

1-Dimethylaminomethylene-3-(3-cyano-phenyl)-thiourea

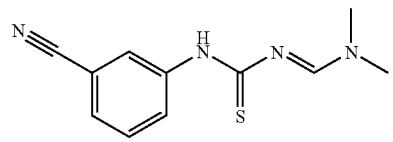

A mixture of 3 g (16.9 mmol) 1-(3-Cyanophenyl)-2-thiourea and 20 ml N,N-Dimethylformamide dimethyl acetal was heated to 100° C. for 1 h. After evaporation of the volatiles the precipitate was suspended in DCM, filtered and dried to yield 3.56 g (91%) of the title compound.

1-H-NMR (400 MHz-DMSO-d6): δ=10.6 (s, br, 1H, NH), 8.76 (s, 1H, CH), 8.10 (d, br, 2H, Ar—H), 7.48 (s, br, 2H, Ar—H), 3.23 (s, 3H, $CH_3$), 3.08 (s, 3H, $CH_3$).

MS (m/e): 233.1 (M+H, 100%)

Example E

1-Dimethylaminomethylene-3-pyridin-3-yl-thiourea

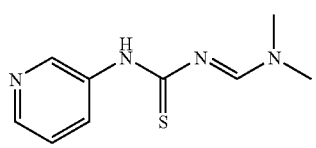

The title compound, MS (m/e): 209.2 (M+H, 100%), was synthesised according to the procedure in Example 4 from pyridin-3-yl-thiourea and dimethylformamide dimethyl acetal.

Example F

1-Dimethylaminomethylene-3-pyridin-4-yl-thiourea

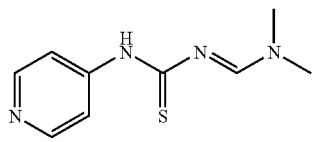

The title compound, MS (m/e): 209.2 (M+H, 100%), was synthesised according to the procedure in Example 4 from pyridin-4-yl-thiourea and dimethylformamide dimethyl acetal.

Example G

1-Dimethylaminomethylene-3-(3-bromo-phenyl)-thiourea

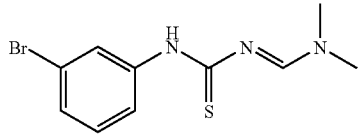

The title compound, MS (m/e): 286.2 (M+H, 100%), was synthesised according to the procedure in Example 4 from 3-bromophenyl-thiourea and dimethylformamide dimethyl acetal.

Example H

1-Dimethylaminomethylene-3-(3-acetyl-phenyl)-thiourea

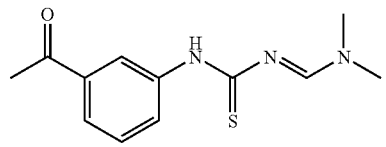

The title compound, MS (m/e): 250.3 (M+H, 100%), was synthesised according to the procedure in Example 4 from 3-acetylphenyl-thiourea and dimethylformamide dimethyl acetal.

Example I

1-Dimethylaminomethylene-3-(3-acetyl-phenyl)-thiourea

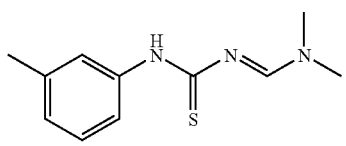

The title compound, MS (m/e): 222.3 (M+H, 100%), was synthesised according to the procedure in Example 4 from 3-methylphenyl-thiourea and dimethylformamide dimethyl acetal.

Example J

2-Bromo-1-(3-ethyl-pyrazin-2-yl)-ethanone dihydrobromide

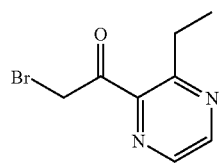

To a solution of 6 g (40 mmol) 1-(3-Ethyl-pyrazin-2-yl)-ethanone in 21 ml HBr (33%) and 7 ml methanol was added 2 ml (40 mmol) bromine and the mixture was heated to 60° C. for 3 h. After removal of the volatiles under reduced pressure the residue was washed with diethyl ether and ethyl acetate. 6.4 g (41%) of the title compound was obtained as grey solid.

MS (m/e): 229.1 (M+H, 100%).

Example K

2-Bromo-1-(3-methyl-pyrazin-2-yl)-ethanone dihydrobromide

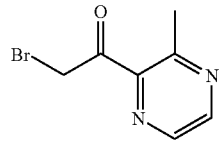

The title compound was synthesised according to Example 4 from 1-(3-Methyl-pyrazin-2-yl)-ethanone and HBr/bromine in 55% yield as grey solid. MS (m/e): 215.0 (M+H, 100%).

Example L

2-Bromo-1-(4-methyl-pyridin-3-yl)-ethanone hydrobromide

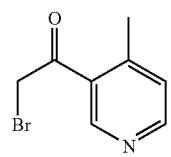

The title compound was synthesised according to Example 4 1-(4-methyl-pyridin-3-yl)-ethanone and HBr/bromine in 85% yield as grey solid. MS (m/e): 214.0 (M+H, 100%).

Example M

2-Bromo-1-(2-ethyl-phenyl)-ethanone

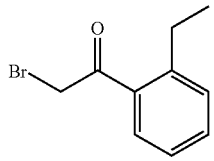

To a solution of 15.2 g (88 mmol) dibromethane in 120 ml THF at −75° C. was added 44 ml (88 mmol) of a 2M solution of LDA in THF and subsequently 6.57 g (40 mmol) ethyl-benzoic acid methyl ester in 80 ml THF. 37.5 ml of a 1.6 M n-butyl lithium solution in n-hexane was added and after 30 min the mixture was treated carefully below −65° C. with 35 ml HCl (37%). The mixture was washed with water and NaHCO$_3$ aq. and the organic phase was dried with MgSO$_4$, filtered and concentrated under reduced pressure. The residue was purified by flash column chromatography on silica eluting with ethyl acetate/hexane 1:9 twice to afford 3.8 g (41%) of the title compound as yellow oil. MS (m/e): 227.1 (M+H, 100%).

Example N

3-Thioureido-benzenesulfonamide

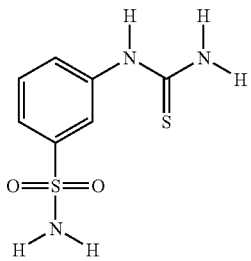

A solution of 10 g (48 mmol) 3-Amino-benzenesulfonamide hydrochloride in 100 ml THF and 8.2 ml (48 mmol) N,N-Diisopropylethylamine was treated with 6.45 ml (48 mmol) benzoyl isothiocyanate and allowed to stir at room temperature. After evaporation to dryness the residue was suspended in diethyl ether. The precipitate was filtered off, dried and suspended in 130 ml methanol and 100 ml THF. K$_2$CO$_3$ (130 mmol) in 45 ml water was added and the mixture was stirred for 60 h at room temperature. The mixture was evaporated to drynes and the residue was treated with water and extracted with ethyl acetate. The combined organic layers were dried with MgSO$_4$ filtered and evaporated to dryness. After suspending the residue in diethyl ether, filtration and drying 8.4 g (76%) of the title compound was obtained as white solid.

1-H-NMR (300 MHz-DMSO-d6): δ=10.0 (s, br, 2H, NH$_2$), 7.94 (d, J=1.7 Hz, 1H, H-2), 7.71 (dd, J=7.7 Hz, J=1.7 Hz, 1H, H-4), 7.56 (m, 2H, H-5/H-6), 7.36 (s, br, 2H, NH$_2$).

MS (m/e): 233.1 (M+H, 100%)

Example O

N-Dimethylaminomethylene-3-(3-dimethylaminomethylene-thioureido)-benzenesulfonamide

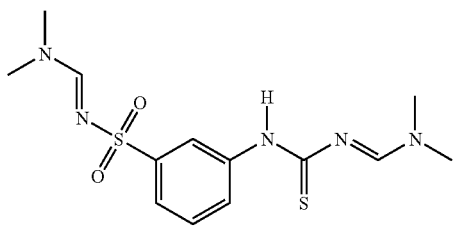

A mixture of 2.3 g (9.9 mmol) 3-Thioureido-benzenesulfonamide and 17 ml N,N-Dimethylformamide dimethyl acetal was heated for 2 h to 90° C. The precipitate was filtered of washed with DCM/diethyl ether 1:3 and dried to yield 2.8 g (82%) of the title compound.

1-H-NMR (300 MHz-DMSO-d6): δ=10.7 (s, br, 2H, NH$_2$), 8.77 (s, 1H, CH), 8.37 (s, br, 1H, CH), 8.17 (s, br, 1H, H-2), 7.58 (m, 1H, H-4), 7.40 (m, 2H, H-5 /H-6).

MS (m/e): 340.2 (M+H, 100%)

Example P 3-(5-Benzoyl-thiazol-2-ylamino)-benzenesulfonamide

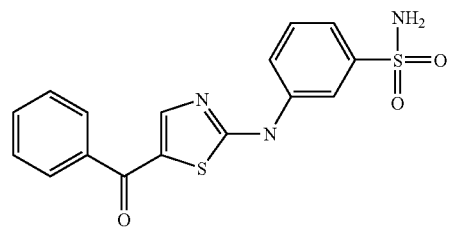

A mixture of 44 mg (0.13 mmol) N-Dimethylaminomethylene-3-(3-dimethylaminomethylene-thioureido)-benzenesulfonamide and 26 mg (0.13 mmol) phenacyl bromide in 0.8 ml DMF was stirred for 16 h at room temperature. 0.12 ml HCl (37%) was added and the mixture was stirred for 69 h at 100° C. After addition of 0.12 ml N,N-Diisopropylethylamine the mixture was subjected to preparative HPLC separation on reversed phase eluting with an acetonitrile/water gradient. Evaporation of the product fractions yielded 6 mg (13%) of the title compound.

1-H-NMR (500 MHz-DMSO): δ=11.25 (s, br, 1H, NH), 8.25 (s, 1H, H-2), 7.90 (s, 1H, thiazole H), 7.85 (m, 3H, Ph), 7.60 (m, 5H, Ph), 7.40 (s, br, 2H, NH$_2$).

MS (m/e): 358 (M−H, 100%)

Example Q (Example 111 in Table)

3-[4-Methyl-5-(2-trifluoromethyl-benzoyl)-thiazol-2-ylamino]-benzonitrile

To a mixture of 801 mg (5 mmol) 3-cyanophenylthioisocyanate in 5 ml 1N NaOH at 0° C. was added 473 mg acetamidine hydrochloride in 10 ml THF and allowed to stir at 0° C. for 16 h. The mixture was extracted with ethylacetate and the combined organic layers were dried with MgSO4 and evaporated to dryness. The residue was purified by flash column chromatography on silica eluting with ethylacetate/cyclohexane 1:2 to yield 510 mg (47%) of 1-(1-Amino-ethylidene)-3-(3-cyano-phenyl)-thiourea. (MS (m/e): 219.2 (M+H, 100%). A mixture of 50 mg (0.23 mmol) 1-(1-Amino-ethylidene)-3-(3-cyano-phenyl)-thiourea, 92 mg (0.345 mmol) 2-Bromo-1-(2-trifluoromethyl-phenyl)-ethanone and 48 ul triethylamine in 1 ml ethanol was stirred for 16 h at room temperature. The mixtures were diluted with methanol and directly subjected to preparative HPLC separation on reversed phase eluting with an acetonitrile/water gradient. Evaporation of the product fractions yielded 10.4 mg (12%) of the title compound. (MS (m/e): 386.2 (M−H, 100%)

According to Example B further aminothiazole derivatives have been synthesised from 1-dimethylaminomethylene-thioureas and α-bromoketones. The results are comprised in the following list embracing Example 1 to Example 97 and Example 112.

According to Example P further aminothiazole derivatives have been synthesised from 1-dimethylaminomethylene-thioureas and α-bromoketones. The results are comprised in the following list embracing Example 98 to Example 110.

| No. | Synthesised from | MW | name | mass found |
|---|---|---|---|---|
| 1 | 1-Dimethylaminomethylene-3-(3-cyano-phenyl)-thiourea and 2-Bromo-1-naphthalen-2-yl-ethanone (commercially available) | 355.4 | 3-[5-(Naphthalene-2-carbonyl)-thiazol-2-ylamino]-benzonitrile | 354.2 M − H |
| 2 | 1-Dimethylaminomethylene-3-(3-cyano-phenyl)-thiourea and phenacyl bromide (commercially available) | 305.4 | 3-(5-Benzoyl-thiazol-2-ylamino)-benzonitrile | 304.1 M − H |
| 3 | 1-Dimethylaminomethylene-3-(3-cyano-phenyl)-thiourea and 2-Bromo-1-p-tolyl-ethanone (commercially available) | 319.4 | 3-[5-(4-Methyl-benzoyl)-thiazol-2-ylamino]-benzonitrile | 318.2 M − H |
| 4 | 1-Dimethylaminomethylene-3-(3-methanesulfonyl-phenyl)-thiourea and phenacyl bromide (commercially available) | 358.4 | [2-(3-Methanesulfonyl-phenylamino)-thiazol-5-yl]-phenyl-methanone | 357.1 M − H |
| 5 | 1-Dimethylaminomethylene-3-(3-methoxy-phenyl)-thiourea (US4532348) and phenacyl bromide (commercially available) | 310.4 | [2-(3-Methoxy-phenylamino)-thiazol-5-yl]-phenyl-methanone | 309.1 M − H |
| 6 | 1-Dimethylaminomethylene-3-(3-trifluoromethyl-phenyl)-thiourea (commercially available) and phenacyl bromide (commercially available) | 348.3 | Phenyl-[2-(3-trifluoromethyl-phenylamino)-thiazol-5-yl]-methanone | 349.3 M + H |
| 7 | 1-Dimethylaminomethylene-3-(3-cyano-phenyl)-thiourea and 2-Bromo-1-(3-methoxy-phenyl)-ethanone (commercially available) | 335.4 | 3-[5-(3-Methoxy-benzoyl)-thiazol-2-ylamino]-benzonitrile | 334.2 M − H |
| 8 | 1-Dimethylaminomethylene-3-(3-cyano-phenyl)-thiourea and 2-Bromo-1-(4-fluoro-phenyl)-ethanone (commercially available) | 323.4 | 3-[5-(4-Fluoro-benzoyl)-thiazol-2-ylamino]-benzonitrile | 322.2 M − H |
| 9 | 1-Dimethylaminomethylene-3-(3-cyano-phenyl)-thiourea and 2-Bromo-1-(4-chloro-phenyl)-ethanone (commercially available) | 339.8 | 3-[5-(4-Chloro-benzoyl)-thiazol-2-ylamino]-benzonitrile | 338.1 M − H |
| 10 | 1-Dimethylaminomethylene-3-(3,5-dichloro-phenyl)-thiourea (commercially available) and 2-Bromo-1-(2-fluoro-phenyl)-ethanone (commercially available) | 367.2 | [2-(3,5-Dichloro-phenylamino)-thiazol-5-yl]-(2-fluoro-phenyl)-methanone | 365.0 M − H |
| 11 | 1-Dimethylaminomethylene-3-(3,5-dichloro-phenyl)-thiourea (commercially | 383.7 | (2-Chloro-phenyl)-[2-(3,5-dichloro-phenylamino)-thiazol-5- | 383.1 M − H |

-continued

| No. | Synthesised from | MW | name | mass found |
|---|---|---|---|---|
| | available) and 2-Bromo-1-(2-chloro-phenyl)-ethanone (commercially available) | | yl]-methanone | |
| 12 | 1-Dimethylaminomethylene-3-(3-cyano-phenyl)-thiourea and 2-Bromo-1-(4-bromo-phenyl)-ethanone (commercially available) | 384.3 | 3-[5-(4-Bromo-benzoyl)-thiazol-2-ylamino]-benzonitrile | 384.1 M − H |
| 13 | 1-Dimethylaminomethylene-3-(3-cyano-phenyl)-thiourea and 2-Bromo-1-(3-chloro-phenyl)-ethanone (commercially available) | 339.8 | 3-[5-(3-Chloro-benzoyl)-thiazol-2-ylamino]-benzonitrile | 338.1 M − H |
| 14 | 1-Dimethylaminomethylene-3-(3-cyano-phenyl)-thiourea and 2-Bromo-1-(2-fluoro-phenyl)-ethanone (commercially available) | 323.4 | 3-[5-(2-Fluoro-benzoyl)-thiazol-2-ylamino]-benzonitrile | 322.2 M − H |
| 15 | 1-Dimethylaminomethylene-3-(3-cyano-phenyl)-thiourea and 2-Bromo-1-(3-fluoro-phenyl)-ethanone (commercially available) | 323.4 | 3-[5-(3-Fluoro-benzoyl)-thiazol-2-ylamino]-benzonitrile | 322.3 M − H |
| 16 | 1-Dimethylaminomethylene-3-(3-cyano-phenyl)-thiourea and 2-Bromo-1-(2-methoxy-phenyl)-ethanone (commercially available) | 335.4 | 3-[5-(2-Methoxy-benzoyl)-thiazol-2-ylamino]-benzonitrile | 334.2 M − H |
| 17 | 1-Dimethylaminomethylene-3-(3-cyano-phenyl)-thiourea and 2-Bromo-1-(3-trifluoromethyl-phenyl)-ethanone (WO0144201) | 373.4 | 3-[5-(3-Trifluoromethyl-benzoyl)-thiazol-2-ylamino]-benzonitrile | 372.2 M − H |
| 18 | 1-Dimethylaminomethylene-3-(3-cyano-phenyl)-thiourea and 2-Bromo-1-(2-chloro-phenyl)-ethanone (commercially available) | 339.8 | 3-[5-(2-Chloro-benzoyl)-thiazol-2-ylamino]-benzonitrile | 338.0 M − H |
| 19 | 1-Dimethylaminomethylene-3-(3-cyano-phenyl)-thiourea and 2-Bromo-1-(3-bromo-phenyl)-ethanone (commercially available) | 384.3 | 3-[5-(3-Bromo-benzoyl)-thiazol-2-ylamino]-benzonitrile | 384.1 M − H |
| 20 | 1-Dimethylaminomethylene-3-(4-chloro-phenyl)-thiourea (commercially available) and 2-Bromo-1-(2-fluoro-phenyl)-ethanone (commercially available) | 332.8 | [2-(4-Chloro-phenylamino)-thiazol-5-yl]-(2-fluoro-phenyl)-methanone | 332.2 M + H |
| 21 | 1-Dimethylaminomethylene-3-(4-chloro-phenyl)-thiourea (commercially available) and 2-Bromo-1-(4-chloro-phenyl)-ethanone (commercially available) | 349.2 | (2-Chloro-phenyl)-[2-(4-chloro-phenylamino)-thiazol-5-yl]-methanone | 349.2 M + H |
| 22 | 1-Dimethylaminomethylene-3-(3-trifluoromethyl-phenyl)-thiourea (commercially available) and 2-Bromo-1-(4-methyl-phenyl)-ethanone (commercially available) | 362.4 | p-Tolyl-[2-(3-trifluoromethyl-phenylamino)-thiazol-5-yl]-methanone | 363.0 M + H |
| 23 | 1-Dimethylaminomethylene-3-(3-trifluoromethyl-phenyl)-thiourea (commercially available) and 2-Bromo-1-(4-fluoro-phenyl)-ethanone (commercially available) | 366.3 | (4-Fluoro-phenyl)-[2-(3-trifluoromethyl-phenylamino)-thiazol-5-yl]-methanone | 367.1 M + H |
| 24 | 1-Dimethylaminomethylene-3-(3-trifluoromethyl-phenyl)-thiourea (commercially available) and 2-Bromo-1-(3-methoxy-phenyl)-ethanone (commercially available) | 378.4 | (3-Methoxy-phenyl)-[2-(3-trifluoromethyl-phenylamino)-thiazol-5-yl]-methanone | 379.2 M + H |

-continued

| No. | Synthesised from | MW | name | mass found |
|---|---|---|---|---|
| 25 | 1-Dimethylaminomethylene-3-(3-trifluoromethyl-phenyl)-thiourea (commercially available) and 2-Bromo-1-(3-chloro-phenyl)-ethanone (commercially available) | 382.8 | (3-Chloro-phenyl)-[2-(3-trifluoromethyl-phenylamino)-thiazol-5-yl]-methanone | 383.2 M + H |
| 26 | 1-Dimethylaminomethylene-3-(3-trifluoromethyl-phenyl)-thiourea (commercially available) and 2-Bromo-1-(2-fluoro-phenyl)-ethanone (commercially available) | 366.3 | (2-Fluoro-phenyl)-[2-(3-trifluoromethyl-phenylamino)-thiazol-5-yl]-methanone | 367.1 M + H |
| 27 | 1-Dimethylaminomethylene-3-(3-trifluoromethyl-phenyl)-thiourea (commercially available) and 2-Bromo-1-(3-fluoro-phenyl)-ethanone (commercially available) | 366.3 | (3-Fluoro-phenyl)-[2-(3-trifluoromethyl-phenylamino)-thiazol-5-yl]-methanone | 367.1 M + H |
| 28 | 1-Dimethylaminomethylene-3-(3-trifluoromethyl-phenyl)-thiourea (commercially available) and 2-Bromo-1-(2-methoxy-phenyl)-ethanone (commercially available) | 378.4 | (2-Methoxy-phenyl)-[2-(3-trifluoromethyl-phenylamino)-thiazol-5-yl]-methanone | 379.2 M + H |
| 29 | 1-Dimethylaminomethylene-3-(3-trifluoromethyl-phenyl)-thiourea (commercially available) and 2-Bromo-1-(2-chloro-phenyl)-ethanone (commercially available) | 382.8 | (2-Chloro-phenyl)-[2-(3-trifluoromethyl-phenylamino)-thiazol-5-yl]-methanone | 383.1 M + H |
| 30 | 1-Dimethylaminomethylene-3-(3-trifluoromethyl-phenyl)-thiourea (commercially available) and 2-Bromo-1-(3-bromo-phenyl)-ethanone (commercially available) | 427.2 | (3-Bromo-phenyl)-[2-(3-trifluoromethyl-phenylamino)-thiazol-5-yl]-methanone | 427.2 M + H |
| 31 | 1-Dimethylaminomethylene-3-pyridin-4-yl-thiourea and 2-Bromo-1-(2-methyl-phenyl)-ethanone (WO9907666) | 295.4 | [2-(Pyridin-4-ylamino)-thiazol-5-yl]-o-tolyl-methanone | 296.2 M + H |
| 32 | 1-Dimethylaminomethylene-3-pyridin-4-yl-thiourea and 2-Bromo-1-(2,4-dichloro-phenyl)-ethanone (commercially available) | 350.2 | (2,4-Dichloro-phenyl)-[2-(pyridin-4-ylamino)-thiazol-5-yl]-methanone | 350.2 M + H |
| 33 | 1-Dimethylaminomethylene-3-pyridin-4-yl-thiourea and 2-Bromo-1-(2,4-dimethyl-phenyl)-ethanone (commercially available) | 309.4 | (2,4-Dimethyl-phenyl)-[2-(pyridin-4-ylamino)-thiazol-5-yl]-methanone | 310.2 M + H |
| 34 | 1-Dimethylaminomethylene-3-pyridin-4-yl-thiourea and 2-Bromo-1-(2-nitro-phenyl)-ethanone (commercially available) | 326.3 | (2-Nitro-phenyl)-[2-(pyridin-4-ylamino)-thiazol-5-yl]-methanone | 327.2 M + H |
| 35 | 1-Dimethylaminomethylene-3-(3-cyano-phenyl)-thiourea and 2-Bromo-1-pyridin-2-yl-ethanone (commercially available) | 306.3 | 3-[5-(Pyridine-2-carbonyl)-thiazol-2-ylamino]-benzonitrile | 307.2 M + H |
| 36 | 1-Dimethylaminomethylene-3-(3-cyano-phenyl)-thiourea and 2-Bromo-1-pyridin-3-yl-ethanone (commercially available) | 306.3 | 3-[5-(Pyridine-3-carbonyl)-thiazol-2-ylamino]-benzonitrile | 307.2 M + H |
| 37 | 1-Dimethylaminomethylene-3-(3-cyano-phenyl)-thiourea | 306.3 | 3-[5-(Pyridine-4-carbonyl)-thiazol-2- | 307.2 M + H |

-continued

| No. | Synthesised from | MW | name | mass found |
|---|---|---|---|---|
| | and 2-Bromo-1-pyridin-4-yl-ethanone (commercially available) | | ylamino]-benzonitrile | |
| 38 | 1-Dimethylaminomethylene-3-(3-cyano-phenyl)-thiourea and 2-Bromo-1-(2-methyl-phenyl)-ethanone (WO9907666) | 319.4 | 3-[5-(2-Methyl-benzoyl)-thiazol-2-ylamino]-benzonitrile | 320.3 M + H |
| 39 | 1-Dimethylaminomethylene-3-(3-cyano-phenyl)-thiourea and 2-Bromo-1-(cyclohexyl)-ethanone (WO9940088) | 311.4 | 3-(5-Cyclohexanecarbonyl-thiazol-2-ylamino)-benzonitrile | 312.2 M + H |
| 40 | 1-Dimethylaminomethylene-3-(3-cyano-phenyl)-thiourea and 2-Bromo-1-(2,4-dichloro-phenyl)-ethanone (commercially available) | 374.3 | 3-[5-(2,4-Dichloro-benzoyl)-thiazol-2-ylamino]-benzonitrile | 374.2 M + H |
| 41 | 1-Dimethylaminomethylene-3-(3-cyano-phenyl)-thiourea and 2-Bromo-1-(2,4-dimethyl-phenyl)-ethanone (commercially available) | 333.4 | 3-[5-(2,4-Dimethyl-benzoyl)-thiazol-2-ylamino]-benzonitrile | 334.2 M + H |
| 42 | 1-Dimethylaminomethylene-3-(3-cyano-phenyl)-thiourea and 2-Bromo-1-(2-nitro-phenyl)-ethanone (commercially available) | 350.4 | 3-[5-(2-Nitro-benzoyl)-thiazol-2-ylamino]-benzonitrile | 351.3 M + H |
| 43 | 1-Dimethylaminomethylene-3-(3-metoxy-phenyl)-thiourea (US4532348) and 2-Bromo-1-(2-fluoro-phenyl)-ethanone (commercially available) | 328.4 | (2-Fluoro-phenyl)-[2-(3-methoxy-phenylamino)-thiazol-5-yl]-methanone | 327.2 M − H |
| 44 | 1-Dimethylaminomethylene-3-(3-metoxy-phenyl)-thiourea (US4532348) and 2-Bromo-1-(2-methyl-phenyl)-ethanone (WO9907666) | 324.4 | [2-(3-Methoxy-phenylamino)-thiazol-5-yl]-o-tolyl-methanone | 323.3 M − H |
| 45 | 1-Dimethylaminomethylene-3-(3-metoxy-phenyl)-thiourea (US4532348) and 2-Bromo-1-(2,4-dimethyl-phenyl)-ethanone (commercially available) | 338.4 | (2,4-Dimethyl-phenyl)-[2-(3-methoxy-phenylamino)-thiazol-5-yl]-methanone | 337.1 M − H |
| 46 | 1-Dimethylaminomethylene-3-(3-metoxy-phenyl)-thiourea (US4532348) and 2-Bromo-1-(2-nitro-phenyl)-ethanone (commercially available) | 355.4 | [2-(3-Methoxy-phenylamino)-thiazol-5-yl]-(2-nitro-phenyl)-methanone | 354.1 M − H |
| 47 | 1-Dimethylaminomethylene-3-(3-trifluoromethyl-phenyl)-thiourea (commercially available) and 2-Bromo-1-pyridin-4-yl-ethanone (commercially available) | 349.3 | Pyridin-4-yl-[2-(3-trifluoromethyl-phenylamino)-thiazol-5-yl]-methanone | 348.2 M − H |
| 48 | 1-Dimethylaminomethylene-3-(3-trifluoromethyl-phenyl)-thiourea (commercially available) and 2-Bromo-1-(2-methyl-phenyl)-ethanone (commercially available) | 362.4 | o-Tolyl-[2-(3-trifluoromethyl-phenylamino)-thiazol-5-yl]-methanone | 361.1 M − H |
| 49 | 1-Dimethylaminomethylene-3-(3-trifluoromethyl-phenyl)-thiourea (commercially available) and 2-Bromo-1-(cyclohexyl)-ethanone (WO9940088) | 354.4 | Cyclohexyl-[2-(3-trifluoromethyl-phenylamino)-thiazol-5-yl]-methanone | 353.2 M − H |
| 50 | 1-Dimethylaminomethylene-3-(3-trifluoromethyl-phenyl)-thiourea (commercially available) and | 417.2 | (2,4-Dichloro-phenyl)-[2-(3-trifluoromethyl-phenylamino)-thiazol-5-yl]-methanone | 417.2 M − H |

-continued

| No. | Synthesised from | MW | name | mass found |
|---|---|---|---|---|
| | 2-Bromo-1-(2,4-dichloro-phenyl)-ethanone (commercially available) | | | |
| 51 | 1-Dimethylaminomethylene-3-(3-trifluoromethyl-phenyl)-thiourea (commercially available) and 2-Bromo-1-(2,4-methyl-phenyl)-ethanone (commercially available) | 376.4 | (2,4-Dimethyl-phenyl)-[2-(3-trifluoromethyl-phenylamino)-thiazol-5-yl]-methanone | 375.3 M − H |
| 52 | 1-Dimethylaminomethylene-3-(3-trifluoromethyl-phenyl)-thiourea (commercially available) and 2-Bromo-1-(2-nitro-phenyl)-ethanone (commercially available) | 393.3 | (2-Nitro-phenyl)-[2-(3-trifluoromethyl-phenylamino)-thiazol-5-yl]-methanone | 392.1 M − H |
| 53 | 1-Dimethylaminomethylene-3-(3-fluoro-phenyl)-thiourea (commercially available) and 2-Bromo-1-(2-fluoro-phenyl)-ethanone (commercially available) | 316.3 | (2-Fluoro-phenyl)-[2-(3-fluoro-phenylamino)-thiazol-5-yl]-methanone | 317.2 M + H |
| 54 | 1-Dimethylaminomethylene-3-(3-fluoro-phenyl)-thiourea (commercially available) and 2-Bromo-1-(2-methyl-phenyl)-ethanone (WO9907666) | 312.4 | [2-(3-Fluoro-phenylamino)-thiazol-5-yl]-o-tolyl-methanone | 313.2 M + H |
| 55 | 1-Dimethylaminomethylene-3-(3-fluoro-phenyl)-thiourea (commercially available) and 2-Bromo-1-(2-chloro-phenyl)-ethanone (commercially available) | 332.8 | (2-Chloro-phenyl)-[2-(3-fluoro-phenylamino)-thiazol-5-yl]-methanone | 333.2 M + H |
| 56 | 1-Dimethylaminomethylene-3-(3-bromo-phenyl)-thiourea and phenacyl bromide (commercially available) | 359.2 | [2-(3-Bromo-phenylamino)-thiazol-5-yl]-phenyl-methanone | 361.1 M + H |
| 57 | 1-Dimethylaminomethylene-3-(3-bromo-phenyl)-thiourea and 2-Bromo-1-(2-methyl-phenyl)-ethanone (WO9907666) | 373.3 | [2-(3-Bromo-phenylamino)-thiazol-5-yl]-o-tolyl-methanone | 373.0 M + H |
| 58 | 1-Dimethylaminomethylene-3-(3-bromo-phenyl)-thiourea and 2-Bromo-1-(2-chloro-phenyl)-ethanone (commercially available) | 393.7 | [2-(3-Bromo-phenylamino)-thiazol-5-yl]-(2-chloro-phenyl)-methanone | 393.4 M + H |
| 59 | 1-Dimethylaminomethylene-3-(3-bromo-phenyl)-thiourea and 2-Bromo-1-(2,4-dimethyl-phenyl)-ethanone (commercially available) | 387.3 | [2-(3-Bromo-phenylamino)-thiazol-5-yl]-(2,4-dimethyl-phenyl)-methanone | 387.2 M + H |
| 60 | 1-Dimethylaminomethylene-3-(3-acetyl-phenyl)-thiourea and 2-Bromo-1-(2-fluoro-phenyl)-ethanone (commercially available) | 340.4 | 1-{3-[5-(2-Fluoro-benzoyl)-thiazol-2-ylamino]-phenyl}-ethanone | 341.2 M + H |
| 61 | 1-Dimethylaminomethylene-3-(3-acetyl-phenyl)-thiourea and 2-Bromo-1-(2-methyl-phenyl)-ethanone (WO9907666) | 336.4 | 1-{3-[5-(2-Methyl-benzoyl)-thiazol-2-ylamino]-phenyl}-ethanone | 337.2 M + H |
| 62 | 1-Dimethylaminomethylene-3-(3-acetyl-phenyl)-thiourea and 2-Bromo-1-(2-fluoro-phenyl)-ethanone (commercially available) | 356.8 | 1-{3-[5-(2-Chloro-benzoyl)-thiazol-2-ylamino]-phenyl}-ethanone | 357.2 M + H |
| 63 | 1-Dimethylaminomethylene-3-(3-acetyl-phenyl)-thiourea and 2-Bromo-1-(2,4-dimethyl-phenyl)-ethanone (commercially available) | 350.4 | 1-{3-[5-(2,4-Dimethyl-benzoyl)-thiazol-2-ylamino]-phenyl}-ethanone | 351.3 M + H |

-continued

| No. | Synthesised from | MW | name | mass found |
|---|---|---|---|---|
| 64 | 1-Dimethylaminomethylene-3-pyridin-3-yl-thiourea and 2-Bromo-1-(2-fluoro-phenyl)-ethanone (commercially available) | 299.3 | (2-Fluoro-phenyl)-[2-(pyridin-3-ylamino)-thiazol-5-yl]-methanone | 300.4 M + H |
| 65 | 1-Dimethylaminomethylene-3-pyridin-3-yl-thiourea and 2-Bromo-1-(2-methyl-phenyl)-ethanone (WO9907666) | 295.4 | [2-(Pyridin-3-ylamino)-thiazol-5-yl]-o-tolyl-methanone | 296.3 M + H |
| 66 | 1-Dimethylaminomethylene-3-pyridin-3-yl-thiourea and 2-Bromo-1-(2-chloro-phenyl)-ethanone (commercially available) | 315.8 | (2-Chloro-phenyl)-[2-(pyridin-3-ylamino)-thiazol-5-yl]-methanone | 316.2 M + H |
| 67 | 1-Dimethylaminomethylene-3-(3-cyano-phenyl)-thiourea and 2-Bromo-1-(3-methyl-pyrazin-2-yl)-ethanone dihydrobromide | 321.4 | 3-[5-(3-Methyl-pyrazine-2-carbonyl)-thiazol-2-ylamino]-benzonitrile | 320.2 M − H |
| 68 | 1-Dimethylaminomethylene-3-(3-cyano-phenyl)-thiourea and 2-Bromo-1-(3-methyl-pyrazin-2-yl)-ethanone dihydrobromide | 335.4 | 3-[5-(3-Ethyl-pyrazine-2-carbonyl)-thiazol-2-ylamino]-benzonitrile | 334.2 M − H |
| 69 | 1-Dimethylaminomethylene-3-(3-cyano-phenyl)-thiourea and 2-Bromo-1-(3-methyl-thiophen-2-yl)-ethanone (EO432040) | 325.4 | 3-[5-(3-Methyl-thiophene-2-carbonyl)-thiazol-2-ylamino]-benzonitrile | 324.2 M − H |
| 70 | 1-Dimethylaminomethylene-3-(3-cyano-phenyl)-thiourea and 2-Bromo-1-(2-ethyl-phenyl)-ethanone | 333.4 | 3-[5-(2-Ethyl-benzoyl)-thiazol-2-ylamino]-benzonitrile | 332.2 M − H |
| 71 | 1-Dimethylaminomethylene-3-(3-cyano-phenyl)-thiourea and 2-Bromo-1-(2-trifluoromethyl-phenyl)-ethanone (EP432040) | 373.4 | 3-[5-(2-Trifluoromethyl-benzoyl)-thiazol-2-ylamino]-benzonitrile | 372.2 M − H |
| 72 | 1-Dimethylaminomethylene-3-(3-cyano-phenyl)-thiourea and 2-Bromo-1-(3-methyl-pyridin-2-yl)-ethanone (WO9935130) | 320.4 | 3-[5-(3-Methyl-pyridine-2-carbonyl)-thiazol-2-ylamino]-benzonitrile | 319.1 M − H |
| 73 | 1-Dimethylaminomethylene-3-(3-cyano-phenyl)-thiourea and 2-Bromo-1-(2-methyl-pyridin-3-yl)-ethanone (J. Heterocycl. Chem. 1978, 15, 217) | 320.4 | 3-[5-(2-Methyl-pyridine-3-carbonyl)-thiazol-2-ylamino]-benzonitrile | 319.2 M − H |
| 74 | 1-Dimethylaminomethylene-3-(3-cyano-phenyl)-thiourea and 2-Bromo-1-(2,5-dimethyl-thiophen-3-yl)-ethanone (WO9921845) | 339.4 | 3-[5-(2,5-Dimethyl-thiophene-3-carbonyl)-thiazol-2-ylamino]-benzonitrile | 338.1 M − H |
| 75 | 1-Dimethylaminomethylene-3-(3-trifluoromethyl-phenyl)-thiourea (commercially available) and 2-Bromo-1-(3-methyl-thiophen-2-yl)-ethanone (EO432040) | 368.4 | (3-Methyl-thiophen-2-yl)-[2-(3-trifluoromethyl-phenylamino)-thiazol-5-yl]-methanone | 367.1 M − H |
| 76 | 1-Dimethylaminomethylene-3-(3-trifluoromethyl-phenyl)-thiourea (commercially available) and 2-Bromo-1-(2-ethyl-phenyl)-ethanone | 376.4 | (2-Ethyl-phenyl)-[2-(3-trifluoromethyl-phenylamino)-thiazol-5-yl]-methanone | 375.3 M − H |
| 77 | 1-Dimethylaminomethylene-3-(3-trifluoromethyl-phenyl)-thiourea (commercially available) and 2-Bromo-1-(2-trifluoromethyl-phenyl)-ethanone (EP432040) | 416.3 | (2-Trifluoromethyl-phenyl)-[2-(3-trifluoromethyl-phenylamino)-thiazol-5-yl]-methanone | 415.2 M − H |

-continued

| No. | Synthesised from | MW | name | mass found |
|---|---|---|---|---|
| 78 | 1-Dimethylaminomethylene-3-(3-trifluoromethyl-phenyl)-thiourea (commercially available) and 2-Bromo-1-(3-methyl-pyridin-2-yl)-ethanone (WO9935130) | 363.4 | (3-Methyl-pyridin-2-yl)-[2-(3-trifluoromethyl-phenylamino)-thiazol-5-yl]-methanone | 362.1 M − H |
| 79 | 1-Dimethylaminomethylene-3-(3-trifluoromethyl-phenyl)-thiourea (commercially available) and 2-Bromo-1-(2,5-dimethyl-thiophen-3-yl)-ethanone (WO9921845) | 382.4 | (2,5-Dimethyl-thiophen-3-yl)-[2-(3-trifluoromethyl-phenylamino)-thiazol-5-yl]-methanone | 381.2 M − H |
| 80 | 1-Dimethylaminomethylene-3-(3-methyl-phenyl)-thiourea and 2-Bromo-1-(2-methyl-phenyl)-ethanone (WO9907666) | 308.4 | o-Tolyl-(2-m-tolylamino-thiazol-5-yl)-methanone | 307.2 M − H |
| 81 | 1-Dimethylaminomethylene-3-(3-methyl-phenyl)-thiourea and 2-Bromo-1-(2-ethyl-phenyl)-ethanone | 322.4 | (2-Ethyl-phenyl)-(2-m-tolylamino-thiazol-5-yl)-methanone | 321.2 M − H |
| 82 | 1-Dimethylaminomethylene-3-(3-methyl-phenyl)-thiourea and 2-Bromo-1-(2-trifluoromethyl-phenyl)-ethanone (EP432040) | 362.4 | (2-m-Tolylamino-thiazol-5-yl)-(2-trifluoromethyl-phenyl)-methanone | 361.0 M − H |
| 83 | 1-Dimethylaminomethylene-3-(3-methyl-phenyl)-thiourea and 2-Bromo-1-(2-fluoro-phenyl)-ethanone (commercially available) | 312.4 | (2-Fluoro-phenyl)-(2-m-tolylamino-thiazol-5-yl)-methanone | 311.1 M − H |
| 84 | 1-Dimethylaminomethylene-3-(3-methyl-phenyl)-thiourea and 2-Bromo-1-(2-chloro-phenyl)-ethanone (commercially available) | 328.8 | (2-Chloro-phenyl)-(2-m-tolylamino-thiazol-5-yl)-methanone | 327.1 M − H |
| 85 | 1-Dimethylaminomethylene-3-(3-methyl-phenyl)-thiourea and 2-Bromo-1-(2-methoxy-phenyl)-ethanone (commercially available) | 324.4 | (2-Methoxy-phenyl)-(2-m-tolylamino-thiazol-5-yl)-methanone | 323.2 M − H |
| 86 | 1-Dimethylaminomethylene-3-(3-methyl-phenyl)-thiourea and 2-Bromo-1-(2,5-dimethyl-thiophen-3-yl)-ethanone (WO9921845) | 328.5 | (2,5-Dimethyl-thiophen-3-yl)-(2-m-tolylamino-thiazol-5-yl)-methanone | 327.2 M − H |
| 87 | 1-Dimethylaminomethylene-3-(3-methanesulfonyl-phenyl)-thiourea and 2-Bromo-1-(2-methyl-phenyl)-ethanone (WO9907666) | 372.5 | [2-(3-Methanesulfonyl-phenylamino)-thiazol-5-yl]-o-tolyl-methanone | 371.1 M − H |
| 88 | 1-Dimethylaminomethylene-3-(3-methanesulfonyl-phenyl)-thiourea and 2-Bromo-1-(2-ethyl-phenyl)-ethanone | 386.5 | (2-Ethyl-phenyl)-[2-(3-methanesulfonyl-phenylamino)-thiazol-5-yl]-methanone | 385.1 M − H |
| 89 | 1-Dimethylaminomethylene-3-(3-methanesulfonyl-phenyl)-thiourea and 2-Bromo-1-(2-trifluoromethyl-phenyl)-ethanone (EP432040) | 426.4 | [2-(3-Methanesulfonyl-phenylamino)-thiazol-5-yl]-(2-trifluoromethyl-phenyl)-methanone | 425.2 M − H |
| 90 | 1-Dimethylaminomethylene-3-(3-methanesulfonyl-phenyl)-thiourea and 2-Bromo-1-(2-chloro-phenyl)-ethanone (commercially available) | 392.9 | (2-Chloro-phenyl)-[2-(3-methanesulfonyl-phenylamino)-thiazol-5-yl]-methanone | 391.0 M − H |
| 91 | 1-Dimethylaminomethylene-3-(3-methanesulfonyl-phenyl)-thiourea and 2-Bromo-1-(4-methyl-pyridin-3-yl)-ethanone | 373.5 | [2-(3-Methanesulfonyl-phenylamino)-thiazol-5-yl]-(4-methyl-pyridin-3-yl)-methanone | 372.1 M − H |

| No. | Synthesised from | MW | name | mass found |
|---|---|---|---|---|
| 92 | 1-Dimethylaminomethylene-3-(3-methanesulfonyl-phenyl)-thiourea and 2-Bromo-1-(2,5-dimethyl-thiophen-3-yl)-ethanone (WO9921845) | 392.5 | (2,5-Dimethyl-thiophen-3-yl)-[2-(3-methanesulfonyl-phenylamino)-thiazol-5-yl]-methanone | 391.0 M − H |
| 93 | 1-(2-Cyano-pyridin-4-yl)-3-dimethylaminomethylene-thiourea and 2-Bromo-1-(2-ethyl-phenyl)-ethanone | 334.4 | 4-[5-(2-Ethyl-benzoyl)-thiazol-2-ylamino]-pyridine-2-carbonitrile | 333.1 M − H |
| 94 | 1-(2-Cyano-pyridin-4-yl)-3-dimethylaminomethylene-thiourea and 2-Bromo-1-(3-methyl-pyridin-2-yl)-ethanone (WO9935130) | 321.4 | 4-[5-(3-Methyl-pyridine-2-carbonyl)-thiazol-2-ylamino]-pyridine-2-carbonitrile | 320.2 M − H |
| 95 | 1-(2-Cyano-pyridin-4-yl)-3-dimethylaminomethylene-thiourea and 2-Bromo-1-(2-methyl-phenyl)-ethanone (WO9907666) | 320.4 | 4-[5-(2-Methyl-benzoyl)-thiazol-2-ylamino]-pyridine-2-carbonitrile | 319.1 M − H |
| 96 | 1-(2-Cyano-pyridin-4-yl)-3-dimethylaminomethylene-thiourea and 2-Bromo-1-(2-chloro-phenyl)-ethanone (commercially available) | 340.8 | 4-[5-(2-Chloro-benzoyl)-thiazol-2-ylamino]-pyridine-2-carbonitrile | 339.0 M − H |
| 97 | 1-(2-Cyano-pyridin-4-yl)-3-dimethylaminomethylene-thiourea and 2-Bromo-1-(2-fluoro-phenyl)-ethanone (commercially available) | 324.3 | 4-[5-(2-Fluoro-benzoyl)-thiazol-2-ylamino]-pyridine-2-carbonitrile | 323.3 M − H |
| 98 | N-Dimethylaminomethylene-3-(3-dimethylaminomethylene-thioureido)-benzenesulfonamide and 2-Bromo-1-(2-methyl-phenyl)-ethanone (WO9907666) | 373.5 | 3-[5-(2-Methyl-benzoyl)-thiazol-2-ylamino]-benzenesulfonamide | 372.1 M − H |
| 99 | N-Dimethylaminomethylene-3-(3-dimethylaminomethylene-thioureido)-benzenesulfonamide and 2-Bromo-1-(2-ethyl-phenyl)-ethanone | 387.5 | 3-[5-(2-Ethyl-benzoyl)-thiazol-2-ylamino]-benzenesulfonamide | 386.1 M − H |
| 100 | N-Dimethylaminomethylene-3-(3-dimethylaminomethylene-thioureido)-benzenesulfonamide and 2-Bromo-1-(4-hydroxy-2-methyl-phenyl)-ethanone (EP1104760) | 389.5 | 3-[5-(4-Hydroxy-2-methyl-benzoyl)-thiazol-2-ylamino]-benzenesulfonamide | 388.1 M − H |
| 101 | N-Dimethylaminomethylene-3-(3-dimethylaminomethylene-thioureido)-benzenesulfonamide and 2-Bromo-1-(2-trifluoromethyl-phenyl)-ethanone (EP432040) | 427.4 | 3-[5-(2-Trifluoromethyl-benzoyl)-thiazol-2-ylamino]-benzenesulfonamide | 427.4 M − H |
| 102 | N-Dimethylaminomethylene-3-(3-dimethylaminomethylene-thioureido)-benzenesulfonamide and 2-Bromo-1-(2-fluoro-phenyl)-ethanone (commercially available) | 377.4 | 3-[5-(2-Fluoro-benzoyl)-thiazol-2-ylamino]-benzenesulfonamide | 376.2 M − H |
| 103 | N-Dimethylaminomethylene-3-(3- | 393.9 | 3-[5-(2-Chloro-benzoyl)-thiazol-2-ylamino]-benzenesulfonamide | 392.0 M − H |

-continued

| No. | Synthesised from | MW | name | mass found |
|---|---|---|---|---|
| | dimethylaminomethylene-thioureido)-benzenesulfonamide and 2-Bromo-1-(2-chloro-phenyl)-ethanone (commercially available) | | | |
| 104 | N-Dimethylaminomethylene-3-(3-dimethylaminomethylene-thioureido)-benzenesulfonamide and 2-Bromo-1-(2-methoxy-phenyl)-ethanone (commercially available) | 389.5 | 3-[5-(2-Methoxy-benzoyl)-thiazol-2-ylamino]-benzenesulfonamide | 388.1 M − H |
| 105 | N-Dimethylaminomethylene-3-(3-dimethylaminomethylene-thioureido)-benzenesulfonamide and 2-Bromo-1-(3-fluoro-phenyl)-ethanone (commercially available) | 377.4 | 3-[5-(3-Fluoro-benzoyl)-thiazol-2-ylamino]-benzenesulfonamide | 376.2 M − H |
| 106 | N-Dimethylaminomethylene-3-(3-dimethylaminomethylene-thioureido)-benzenesulfonamide and 2-Bromo-1-(3-chloro-phenyl)-ethanone (commercially available) | 393.9 | 3-[5-(3-Chloro-benzoyl)-thiazol-2-ylamino]-benzenesulfonamide | 392.0 M − H |
| 107 | N-Dimethylaminomethylene-3-(3-dimethylaminomethylene-thioureido)-benzenesulfonamide and 2-Bromo-1-(4-methyl-pyridin-3-yl)-ethanone | 374.4 | 3-[5-(4-Methyl-pyridine-3-carbonyl)-thiazol-2-ylamino]-benzenesulfonamide | 373.1 M − H |
| 108 | N-Dimethylaminomethylene-3-(3-dimethylaminomethylene-thioureido)-benzenesulfonamide and 2-Bromo-1-(3-methyl-pyridin-2-yl)-ethanone | 374.4 | 3-[5-(3-Methyl-pyridine-2-carbonyl)-thiazol-2-ylamino]-benzenesulfonamide | 373.1 M − H |
| 109 | N-Dimethylaminomethylene-3-(3-dimethylaminomethylene-thioureido)-benzenesulfonamide and 2-Bromo-1-(3-ethyl-pyrazin-2-yl)-ethanone dihydrobromide | 389.5 | 3-[5-(3-Ethyl-pyrazine-2-carbonyl)-thiazol-2-ylamino]-benzenesulfonamide | 387.8 M − H |
| 110 | N-Dimethylaminomethylene-3-(3-dimethylaminomethylene-thioureido)-benzenesulfonamide and 2-Bromo-1-(3-methyl-thiophen-2-yl)-ethanone (EO432040) | 379.5 | 3-[5-(3-Methyl-thiophene-2-carbonyl)-thiazol-2-ylamino]-benzenesulfonamide | 378.1 M − H |
| 111 | (see Example Q) | | 3-[4-Methyl-5-(2-trifluoromethyl-benzoyl)-thiazol-2-ylamino]-benzonitrile | |
| 112 | 1-Dimethylaminomethylene-3-(3-methyl-phenyl)-thiourea and | | Phenyl-(2-m-tolylamino-thiazol-5-yl)-methanone | 293.2 M − H |

| No. | Synthesised from | MW | name | mass found |
|---|---|---|---|---|
| | phenacylbromide (commercially available) | | | |

Example A

A compound of formula I can be used in a manner known per se as the active ingredient for the production of tablets of the following composition:

| | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Example B

A compound of formula I can be used in a manner known per se as the active ingredient for the production of capsules of the following composition:

| | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| | 220.0 mg |

What is claimed is:

1. A compound of formula I:

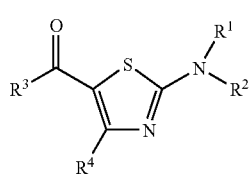

(I)

wherein:

$R^1$ is aryl or heteroaryl, wherein at least one of the two meta positions of each aryl and heteroaryl group is substituted with $R^5$;

$R^2$ is hydrogen, alkyl or cycloalkyl;

$R^3$ is cycloalkyl or aryl, wherein at least one of the two ortho positions of each cycloalkyl or aryl group is substituted with $R^6$;

$R^4$ is hydrogen, alkyl or cycloalkyl;

$R^5$ is cyano, trifluoromethyl, alkyl-$SO_2$—, amino-$SO_2$—, or alkylcarbonyl; and $R^6$ is hydrogen, halogen, cyano, nitro, trifluoromethyl, alkyl, alkoxy, hydroxy or alkoxycarbonyl;

or a pharmaceutically acceptable salt or ester thereof.

2. The compound according to claim 1, wherein $R^5$ is selected from cyano, trifluoromethyl, methyl-$SO_2$—, $NH_2$—$SO_2$— and methylcarbonyl.

3. The compound according to claim 1 selected from

3-[5-(2-Fluoro-benzoyl)-thiazol-2-ylamino]-benzonitrile;

3-[5-(2-Chloro-benzoyl)-thiazol-2-ylamino]-benzonitrile;

(2-Chloro-phenyl)-[2-(3-trifluoromethyl-phenylamino)-thiazol-5-yl]-methanone;

3-[5-(2-Methyl-benzoyl)-thiazol-2-ylamino]-benzonitrile;

o-Tolyl-[2-(3-trifluoromethyl-phenylamino)-thiazol-5-yl]-methanone;

1-{3-[5-(2-Methyl-benzoyl)-thiazol-2-ylamino]-phenyl}-ethanone;

3-[5-(2-Ethyl-benzoyl)-thiazol-2-ylamino]-benzonitrile;

3-[5-(2-Trifluoromethyl-benzoyl)-thiazol-2-ylamino]-benzonitrile;

[2-(3-Methanesulfonyl-phenylamino)-thiazol-5-yl]-o-tolyl-methanone;

(2-Ethyl-phenyl)-[2-(3-methanesulfonyl-phenylamino)-thiazol-5-yl]-methanone;

4-[5-(2-Ethyl-benzoyl)-thiazol-2-ylamino]-pyridine-2-carbonitrile;

4-[5-(2-Methyl-benzoyl)-thiazol-2-ylamino]-pyridine-2-carbonitrile;

3-[5-(2-Ethyl-benzoyl)-thiazol-2-ylamino]-benzenesulfonamide; and

3-[5-(2-Trifluoromethyl-benzoyl)-thiazol-2-ylamino]-benzenesulfonamide.

4. A method for the treatment of obesity in a patient in need of said treatment, which comprises administering to said patient an effective amount of a compound of claim 1.

5. The method according to claim 4, wherein said compound is administered orally in an amount of from about 0.1 mg to 20 mg per kg per day.

6. A pharmaceutical composition, comprising a therapeutically effective amount of a compound according to claim 1, a therapeutically inert carrier and a therapeutically effective amount of orlistat.

* * * * *